United States Patent
Yoshida et al.

(10) Patent No.: US 7,598,254 B2
(45) Date of Patent: Oct. 6, 2009

(54) SUBSTITUTED 1,3-THIAZOLO[5,4-D]PYRIMIDINES AS XANTHINE OXIDASE INHIBITORS

(75) Inventors: Shinichi Yoshida, Chiba (JP); Kunio Kobayashi, Saitama (JP); Nobutaka Mochiduki, Chiba (JP); Tomio Yamakawa, Chiba (JP); Tadashi Kobayashi, Tokyo (JP); Yoriko Shinohara, Chiba (JP)

(73) Assignee: Nippon Chemiphar Co., Ltd., Chiyoda-ku, Tokyo (JP)

( * ) Notice: Subject to any disclaimer, the term of this patent is extended or adjusted under 35 U.S.C. 154(b) by 380 days.

(21) Appl. No.: 11/629,277

(22) PCT Filed: Jun. 13, 2005

(86) PCT No.: PCT/JP2005/011188

§ 371 (c)(1),
(2), (4) Date: Dec. 13, 2006

(87) PCT Pub. No.: WO2005/121153

PCT Pub. Date: Dec. 22, 2005

(65) Prior Publication Data

US 2007/0293512 A1 Dec. 20, 2007

(30) Foreign Application Priority Data

Jun. 14, 2004 (JP) .............................. 2004-175798

(51) Int. Cl.
*C07D 513/04* (2006.01)
*A61K 31/519* (2006.01)
*A61P 19/06* (2006.01)
*C07D 515/04* (2006.01)

(52) U.S. Cl. .................................... 514/260.1; 544/255
(58) Field of Classification Search ................. 544/255; 514/260.1
See application file for complete search history.

(56) References Cited

U.S. PATENT DOCUMENTS 7,253,154 B2 * 8/2007 Yoshida et al. ................. 514/81
2007/0265283 A1 * 11/2007 Yoshida et al. ........... 514/263.1

OTHER PUBLICATIONS

Falco et. al., JACS, 1952, 74, 4897-4902.*

* cited by examiner

*Primary Examiner*—James O Wilson
*Assistant Examiner*—Susanna Moore
(74) *Attorney, Agent, or Firm*—Nixon Peabody LLP; Jeffrey L. Costellia

(57) ABSTRACT

The invention relates to compounds of the following formula (I) or their salts:

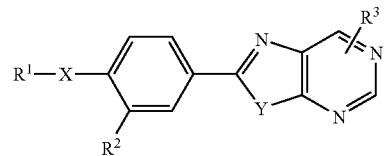

in which $R^1$ is a group of phenyl, naphthyl, pyridyl or the like which may have a substituent such as an alkyl group having 1-8 carbon atoms, an alkoxy group having 1-8 carbon atoms, an alkoxycarbonyl group having 2-8 carbon atoms, carboxyl, halogen, hydroxyl, nitro, or cyano; $R^2$ is cyano, nitro, or the like; $R^3$ is hydroxyl or the like; X is oxygen, sulfur, or the like; and Y is oxygen or sulfur, and a xanthine oxidase inhibitor containing the compound.

13 Claims, No Drawings

SUBSTITUTED 1,3-THIAZOLO[5,4-D]PYRIMIDINES AS XANTHINE OXIDASE INHIBITORS

FIELD OF THE INVENTION

The present invention relates to a xanthine oxidase inhibitor.

BACKGROUND OF THE INVENTION

The hyperuricemia causes gout and renal insufficiency and further is considered to be a factor causing coronary disease. Furthermore, the hyperuricemia is suggested to closely relate to development of diseases of adult people such as hypertension. Therefore, treatment of the hyperuricemia can be effective not only for treating gout but also for preventing various diseases relating to daily nutrition and developing in the course of advancement of age.

At the present time, the hyperuricemia is treated using an inhibitor for inhibiting production of uremic acid such as allopurinol and an accelerator for uricotelism such as benzbromalone. However, the allopurinol is well known to cause side effects such as lesion, hepatopathy, and myelogenetic troubles. The allopurinol and its metabolic product (oxypurinol) are excreted from kidney. However, if the excretion of uric acid decreases, the excretion of these compounds also decreases and the their concentrations in blood increase. Therefore, the chance of causing side effects increases.

It is reported that benzbromalone also causes hepatopathy. Accordingly, it is desired to develop new pharmaceuticals so that the practitioners can select most appropriate pharmaceuticals.

Recently, the below-mentioned xanthine oxidase inhibitors having no purine nucleus such as TMX-67 (Teijin Corporation, Patent Publication 1: WO 92/09279), Y-700 (Mitsubishi Wellpharma Corporation, Patent Publication 2: WO 98/18765) and KT651 (Kotobuki Corporation, Patent Publication 3: JP-A-12-1431) have been reported:

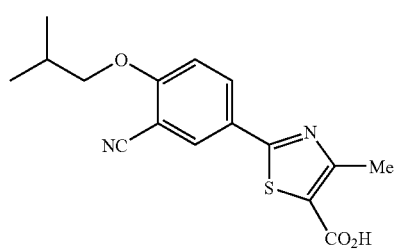

TMX-67

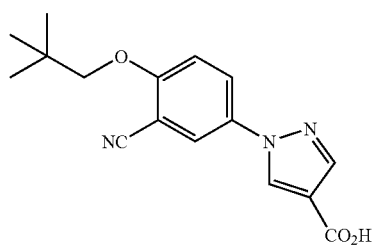

Y-700

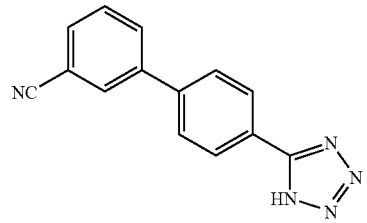

KT651

The present inventors made studies on bicyclic condensed hetero rings having structure differing from the above-mentioned structures and filed a patent application (Patent Publication 4: WO 03/042185).

The inventors further have made studies and discovered that compounds of the below-mentioned formula (I) which are 4-hydroxy-2-phenylthiazolo[5,4-d]pyrimidine or 4-hydroxy-2-phenyloxazolo[5,4-d]pyrimidine in which its phenyl group has cyano in the 3-position and phenoxy or the like in the 4-position have a xanthine oxidase inhibiting effect. The present invention has been completed based on the discovery.

DISCLOSURE OF THE INVENTION

The present invention has an object to provide compounds of the below-mentioned formula (I) which have a xanthine oxidase (XOD) inhibiting effect.

The invention resides in the compounds of the following formula (I) and their salts:

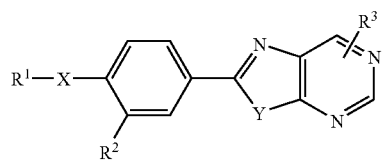

in which $R^1$ represents an aryl group having 6-10 carbon atoms or a hetero-aryl group which may have a substituent selected from the group and atom consisting of an alkyl group having 1-8 carbon atoms, a halogen-substituted alkyl group having 1-8 carbon atoms, an alkoxy group having 1-8 carbon atoms, an alkoxy group having 1-8 carbon atoms which is substituted with an alkoxy group having 1-8 carbon atoms, an alkoxy-carbonyl group having 2-8 carbon atoms, formyl, carboxyl, halogen, hydroxyl, nitro, cyano, amino, an aryl group having 6-10 carbon atoms, and an aryloxy group having 6-10 carbon atoms;

$R^2$ represents cyano, nitro, formyl, carboxyl, carbamoyl, or an alkoxycarbonyl group having 2-8 carbon atoms;

$R^3$ represents hydroxyl, amino, carboxyl, mercapto, $OR^4$ or $NHR^5$ in which each of $R^4$ and $R^5$ is an alkyl group having 1-8 carbon atoms which may have a substituent selected from the group and atom consisting of halogen, hydroxyl, nitro, cyano, amino, an aryl group having 6-10 carbon atoms, and an aryloxy group having 6-10 carbon atoms;

X represents oxygen, $-N(R^6)-$, or $-S(O)_n-$ in which $R^6$ is hydrogen, an alkyl group having 1-8 carbon atoms, or the group for $R^1$, and n is an integer of 0 to 2; and Y represents oxygen or sulfur.

Further, the invention relates to a xanthine oxidase inhibitor containing a compound of the formula (I) or a salt thereof as an active component.

Furthermore, the invention relates to an agent for treating hyperuricemia containing a compound of the formula (I) or a salt thereof as an active component.

PREFERRED EMBODIMENTS OF THE INVENTION

The invention is further described below in detail.

Examples of the alkyl groups having 1-8 carbon atoms which are optionally attachable substituents of the aryl group having 6-10 carbon atoms or hetero-aryl group for $R^4$, $R^5$, $R^6$ and $R^1$ in the formula (I) include methyl, ethyl, propyl, isopropyl, butyl, isobutyl, t-butyl, and pentyl.

Examples of the halogen-substituted alkyl groups having 1-8 carbon atoms which are optionally attachable substituents for the aryl group having 6-10 carbon atoms or hetero-aryl group for $R^1$ include methyl, ethyl, propyl, isopropyl, butyl, isobutyl, t-butyl, and pentyl which has a substituent such as 1-3 fluorine, chlorine, bromine, or the like.

Examples of the alkoxy groups having 1-8 carbon atoms which are optionally attachable substituents for the aryl group having 6-10 carbon atoms or hetero-aryl group for $R^1$ include methoxy, ethoxy, propyloxy, isopropyloxy, butyloxy, isobutyloxy, t-butyloxy, and pentyloxy.

Examples of the alkoxy groups having 1-8 carbon atoms and having an alkoxy substituent having 1-8 carbon atoms which are optionally attachable substituents for the aryl group having 6-10 carbon atoms or hetero-aryl group for $R^1$ include methoxymethoxy.

Examples of the alkoxycarbonyl groups having 2-8 carbon atoms for $R^2$ and the alkoxycarbonyl groups having 2-8 carbon atoms which are optionally attachable substituents and the aryl group having 6-10 carbon atoms or hetero-aryl group for $R^1$ include methoxycarbonyl, ethoxycarbonyl, and propyloxycarbonyl.

Examples of the halogen atoms which are optionally attachable substituents for the aryl group having 6-10 carbon atoms or hetero-aryl group for $R^1$ and also for the alkyl group having 1-8 carbon atoms for $R^4$ and $R^5$ include fluorine, chlorine, and bromine.

Examples of the aryl groups having 6-10 carbon atoms for $R^1$, the aryl groups having 6-10 carbon atoms which are optionally attachable substituents for the aryl or hetero-aryl group for $R^1$, and the aryl groups having 6-10 carbon atoms which are optionally attachable substituents for the alkyl group having 1-8 carbon atoms for $R^4$ and $R^5$ include phenyl and naphthyl.

Examples of the aryloxy group having 6-10 carbon atoms which are optionally attachable substituents for the aryl or heteroaryl group having 6-10 carbon atoms for $R^1$ and also for the alkyl group having 1-8 carbon atoms for $R^4$ and $R^5$ include phenyloxy and naphthyloxy.

Examples of the hetero-aryl group for $R^1$ include furyl, pyrrolyl, thienyl, imidazolyl, pyrimidinyl, thiazolyl, pyridyl, indolyl and quinolyl.

It is preferred that n is 0.

The compound of the formula (I) can be in the form of a pharmacologically acceptable salt. For instance, a salt of an alkali metal such as sodium, potassium, or lithium.

Preferred compounds according to the invention are described below.

(1) The compounds of the formula (I) and salts thereof, in which $R^1$ represents a phenyl, naphthyl, furyl, pyrrolyl, thienyl, imidazolyl, pyrimidinyl, thiazolyl, pyridyl, indolyl or quinolyl group which may have a substituent selected from the group and atom consisting of an alkyl group having 1-8 carbon atoms, a halogen-substituted alkyl group having 1-8 carbon atoms, an alkoxy group having 1-8 carbon atoms, an alkoxycarbonyl group having 2-8 carbon atoms, formyl, carboxyl, halogen, hydroxyl, nitro, cyano, amino, an aryl group having 6-10 carbon atoms, and an aryloxy group having 6-10 carbon atoms.

(2) The compounds of the formula (I) and salts thereof, in which $R^1$ represents a phenyl group which may have a substituent selected from the group and atom consisting of an alkyl group having 1-8 carbon atoms, a halogen-substituted alkyl group having 1-8 carbon atoms, an alkoxy group having 1-8 carbon atoms, an alkoxycarbonyl group having 2-8 carbon atoms, formyl, carboxyl, halogen, hydroxyl, nitro, cyano, amino, an aryl group having 6-10 carbon atoms, and an aryloxy group having 6-10 carbon atoms.

(3) The compounds of the formula (I) and salts thereof, in which $R^1$ represents a phenyl group which may have a substituent selected from the group and atom consisting of an alkyl group having 1-8 carbon atoms, a halogen-substituted alkyl group having 1-8 carbon atoms, an alkoxy group having 1-8 carbon atoms, an alkoxycarbonyl group having 2-8 carbon atoms, formyl, carboxyl, halogen, phenyl, and phenoxy.

(4) The compounds of the formula (I) and salts thereof and the compounds of (1) to (3) above and salts thereof, in which $R^2$ represents cyano or nitro.

(5) The compounds of the formula (I) and salts thereof and the compounds of (1) to (3) above and salts (5) The compounds of the formula (I) and salts thereof and the compounds of (1) to (3) above and salts thereof, in which $R^2$ represents cyano.

(6) The compounds of the formula (I) and salts thereof and the compounds of (1) to (5) above and salts thereof, in which $R^3$ represents hydroxyl.

(7) The compounds of the formula (I) and salts thereof and the compounds of (1) to (6) above and salts thereof, in which $R^3$ is attached to the 4-position of the condensed (bicyclic) hetero ring.

(8) The compounds. of the formula (I) and salts thereof and the compounds of (1) to (7) above and salts thereof, in which X is oxygen, NH, or sulfur.

(9) The compounds of the formula (I) and salts thereof and the compounds of (1) to (7) above and salts thereof, in which X is oxygen.

(10) The compounds of the formula (I) and salts thereof and the compounds of (1) to (9) above and salts thereof, in which Y is sulfur.

Processes for preparing a compound of the formula (I) are illustrated below.

[Synthesis process 1—in the case of Y=S]

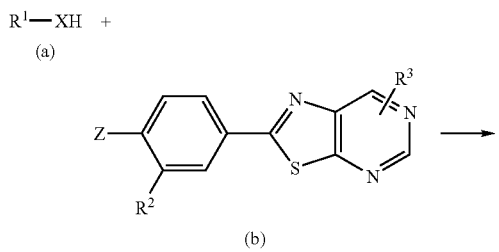

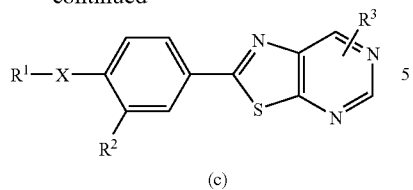

(c)

[in the formula, Z is a halogen atom such as chlorine, and each of $R^1$, $R^2$, $R^3$, and X has the same meaning as above.]

The compound of the invention represented by the formula (c) can be obtained by reacting a compound of the formula (a) and a 2-phenylthiazolo[5,5-d]pyrimidine de- in a such solvent as DMSO at a temperature of from room temperature to 60° C. in the presence of a base such as sodium hydride.

In the case of X=S, the reaction can be carried out by refluxing under heating in a such solvent as ethanol in the presence of a base such as potassium carbonate.

In the case of X=NH, the reaction can be carried out by refluxing under heating in the presence of a base such as copper oxide or potassium carbonate.

The starting compound, i.e., a 2-phenylthiazolo[5,4-d]pyrimidine derivative represented by the formula (b), can be obtained, for instance, by the following process.

Synthesis Process (1) for the Starting Compound

Synthesis Process (2) for the Starting Compound

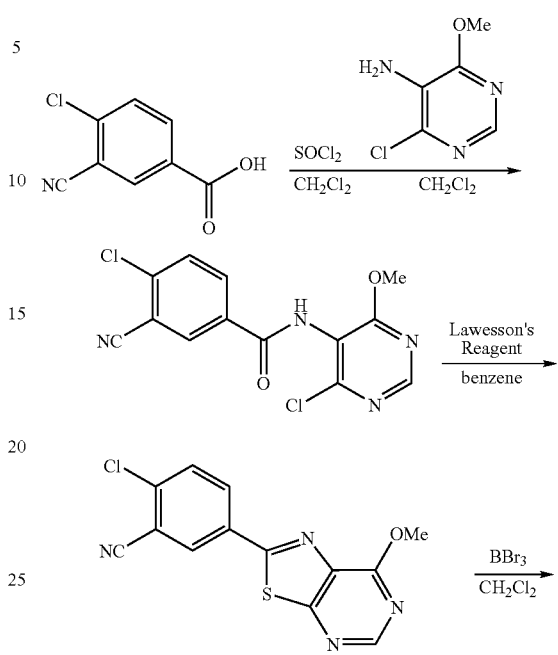

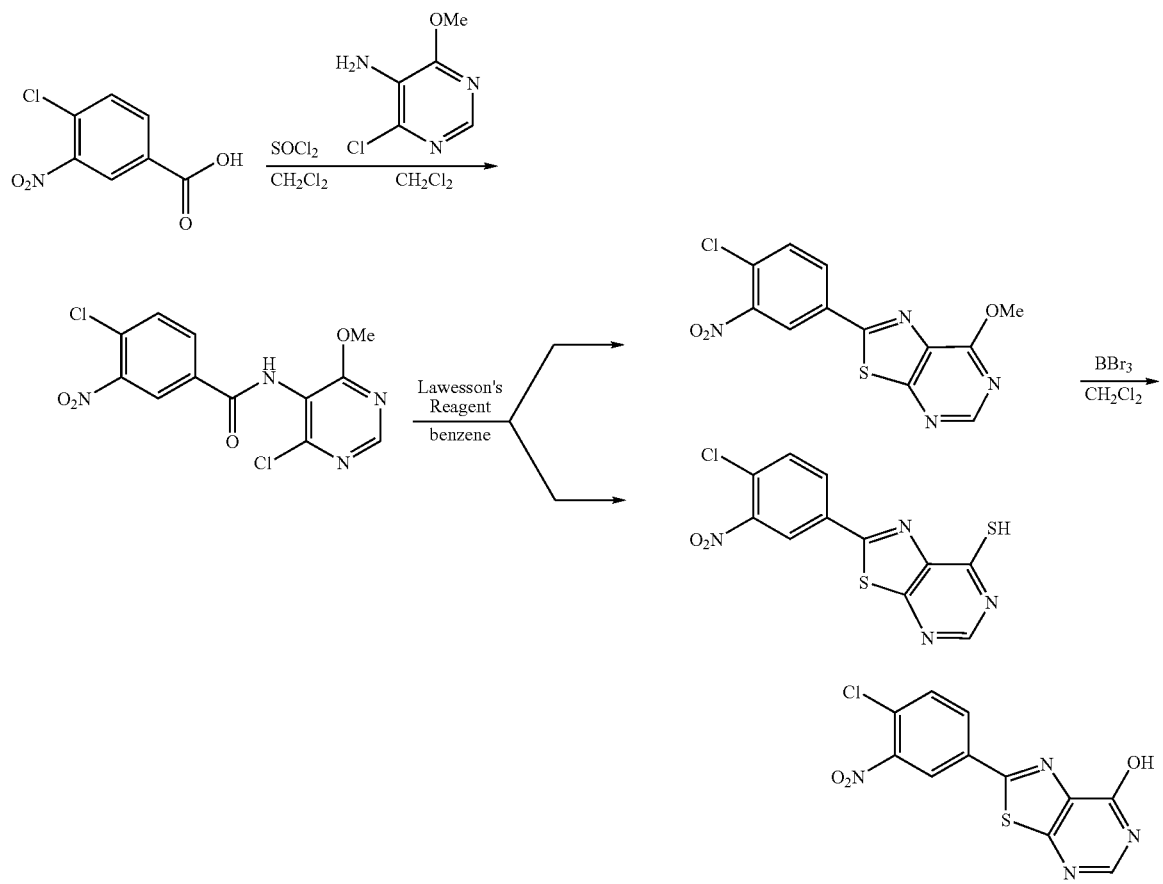

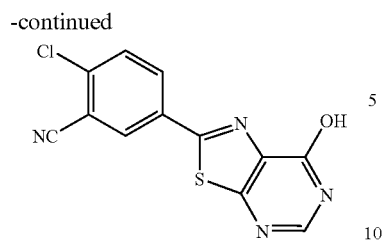

(Synthesis process 2)

In the case of Y=O

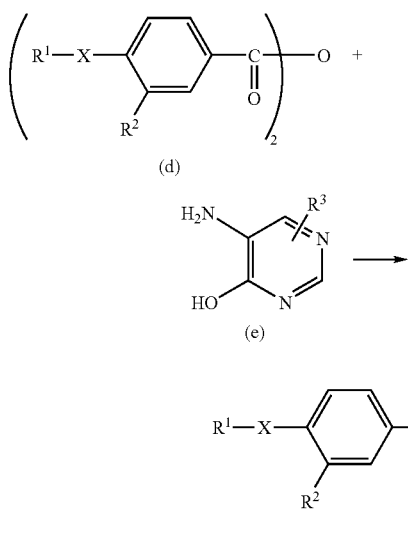

in which each of $R_1$, $R^2$, $R^3$, and X is the same as hereinbefore.

The compound of the invention represented by the formula (f) can be obtained by heating a benzoic anhydride of the formula (d) and a 5-amino-4-hydroxypyrimidine derivative of the formula (e).

The starting compound, i,e., benzoic acid anhydride of the formula (d), can be obtained, for instance, by the following process.

Synthesis (3) of the Starting Compound

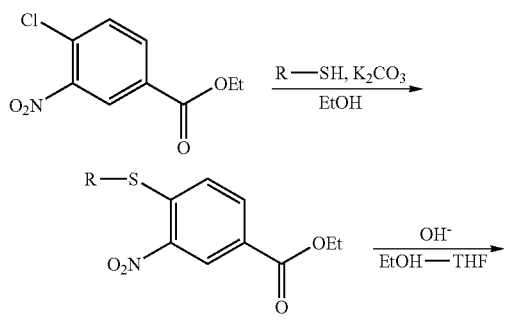

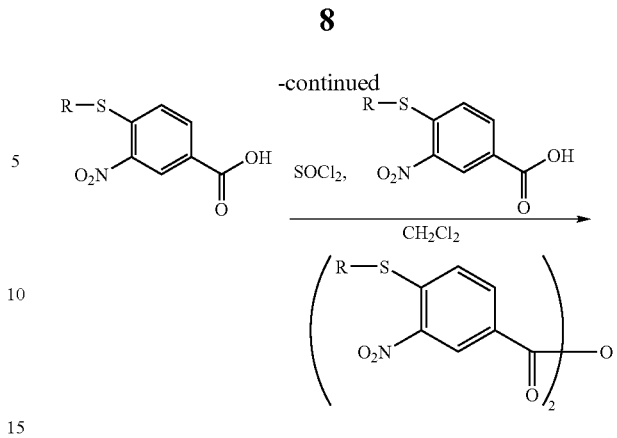

The salt of the compound of the formula (I) in which $R^3$ is OK can be obtained by reacting the compound of the invention in which $R^3$ is hydroxyl with potassium hydroxide in a solvent such as chloroform or methanol The compounds of the invention can be prepared by the above-mentioned synthesis process 1, 2, the working examples described hereinafter, the processes of the Patent Publication 1, etc., and the known processes.

Examples of the compounds of the invention prepared by these processes are set forth in Table 1 to 10:

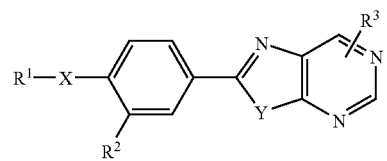

Each of $R^1$, $R^2$, $R^3$, X and Y is described in Tables 1-10.

TABLE 1

| $R^1$ | $R^2$ | $R^3$ 4- | $R^3$ 6- | X | Y |
|---|---|---|---|---|---|
| Cl—⟨phenyl⟩— | NO$_2$ | SH | H | S | S |
| Cl—⟨phenyl⟩— | CN | SH | H | S | S |
| Cl—⟨phenyl⟩— | NO$_2$ | OK | H | S | S |
| Cl—⟨phenyl⟩— | NO$_2$ | OH | H | S | S |
| ⟨phenyl⟩— | NO$_2$ | OH | H | S | S |
| ⟨phenyl⟩— | CN | OH | H | S | S |

TABLE 1-continued

| R¹ | R² | R³ 4- | R³ 6- | X | Y |
|---|---|---|---|---|---|
| 4-Cl-phenyl | NO₂ | OH | H | O | S |
| 4-Cl-phenyl | NO₂ | H | OH | O | S |
| 4-Cl-phenyl | NO₂ | OH | H | O | O |
| 4-Cl-phenyl | NO₂ | OH | H | NH | S |

TABLE 2

| R¹ | R² | R³ 4- | R³ 6- | X | Y |
|---|---|---|---|---|---|
| 4-Cl-phenyl | CHO | OH | H | O | S |
| 4-Cl-phenyl | NO₂ | OH | H | S | O |
| 4-Cl-phenyl | CN | OH | H | S | O |
| phenyl | NO₂ | OH | H | O | S |
| phenyl | CN | OH | H | O | S |
| phenyl | NO₂ | H | OH | O | S |
| phenyl | NO₂ | OH | H | O | O |
| phenyl | CO₂H | OH | H | O | S |
| 4-Cl-phenyl | CN | OH | H | S | S |

TABLE 2-continued

| R¹ | R² | R³ 4- | R³ 6- | X | Y |
|---|---|---|---|---|---|
| 4-Cl-naphthyl | NO₂ | OH | H | O | S |

TABLE 3

| R¹ | R² | R³ 4- | R³ 6- | X | Y |
|---|---|---|---|---|---|
| 4-Cl-naphthyl | CN | OH | H | O | S |
| 4-F-phenyl | NO₂ | OH | H | O | S |
| 4-F-phenyl | CN | OH | H | O | S |
| 4-F-phenyl | NO₂ | H | OH | O | S |
| 4-F-phenyl | NO₂ | OH | H | O | O |
| 4-F-phenyl | NO₂ | OH | H | S | O |
| 4-F-phenyl | NO₂ | OH | H | S | S |
| 4-F-phenyl | NO₂ | OH | H | NH | S |
| 4-F-phenyl | CONH₂ | OH | H | O | S |
| 4-MeO-phenyl | NO₂ | OH | H | O | S |

TABLE 4

| R¹ | R² | R³ 4- | R³ 6- | X | Y |
|---|---|---|---|---|---|
| 4-F-phenyl | NO$_2$ | OH | H | O | S |
| 4-F-phenyl | CN | OH | H | O | S |
| 4-F-phenyl | NO$_2$ | H | OH | O | S |
| 4-F-phenyl | NO$_2$ | OH | H | O | O |
| 4-F-phenyl | NO$_2$ | OH | H | S | O |
| 4-F-phenyl | NO$_2$ | OH | H | S | S |
| 4-F-phenyl | NO$_2$ | OH | H | NH | S |
| 4-F-phenyl | CONH$_2$ | OH | H | O | S |
| 4-MeO-phenyl | NO$_2$ | OH | H | O | S |
| 4-MeO-phenyl | CN | OH | H | O | S |

TABLE 5

| R¹ | R² | R³ 4- | R³ 6- | X | Y |
|---|---|---|---|---|---|
| 2-Cl-phenyl | NO$_2$ | OH | H | S | S |
| 2-Cl-phenyl | NO$_2$ | OH | H | NH | S |
| 2-Cl-phenyl | CO$_2$Et | OH | H | O | S |
| 3-F-phenyl | NO$_2$ | OH | H | O | S |
| 3-F-phenyl | CN | OH | H | O | S |
| 3-F-phenyl | NO$_2$ | H | OH | O | S |
| 3-F-phenyl | NO$_2$ | OH | H | O | O |
| 3-F-phenyl | NO$_2$ | OH | H | S | O |
| 3-F-phenyl | NO$_2$ | OH | H | S | S |
| 3-F-phenyl | NO$_2$ | OH | H | NH | S |

TABLE 6

| R¹ | R² | R³ 4- | R³ 6- | X | Y |
|---|---|---|---|---|---|
| 3-F-phenyl | NO$_2$ | NH$_2$ | H | O | S |

TABLE 6-continued

| R¹ | R² | R³ 4- | R³ 6- | X | Y |
|---|---|---|---|---|---|
| 2-F-phenyl | NO₂ | OH | H | O | S |
| 2-F-phenyl | CN | OH | H | O | S |
| 2-F-phenyl | NO₂ | H | OH | O | S |
| 2-F-phenyl | NO₂ | OH | H | O | O |
| 2-F-phenyl | NO₂ | OH | H | S | O |
| 2-F-phenyl | NO₂ | OH | H | S | S |
| 2-F-phenyl | NO₂ | OH | H | NH | S |
| 2-F-phenyl | NO₂ | CO₂H | H | O | S |
| 4-Cl-phenyl | CN | OH | H | O | S |

TABLE 7

| R¹ | R² | R³ 4- | R³ 6- | X | Y |
|---|---|---|---|---|---|
| 4-Cl-phenyl | CN | H | OH | O | S |

TABLE 7-continued

| R¹ | R² | R³ 4- | R³ 6- | X | Y |
|---|---|---|---|---|---|
| 4-Cl-phenyl | CN | OH | H | O | O |
| 4-Cl-phenyl | CN | OH | H | NH | S |
| 4-Cl-phenyl | CN | NHMe | H | O | S |
| 4-MeO₂C-phenyl | NO₂ | OH | H | O | S |
| 4-MeO₂C-phenyl | CN | OH | H | O | S |
| 4-HO₂C-phenyl | NO₂ | OH | H | O | S |
| 4-HO₂C-phenyl | CN | OH | H | O | S |
| 4-(PhO)-phenyl | NO₂ | OH | H | O | S |
| 4-(PhO)-phenyl | CN | OH | H | O | S |

TABLE 8

| R¹ | R² | R³ 4- | R³ 6- | X | Y |
|---|---|---|---|---|---|
| phenyl | NO₂ | OH | H | NH | S |
| phenyl | CN | OH | H | NH | S |
| 4-iPr-phenyl | NO₂ | OH | H | O | S |
| 4-iPr-phenyl | CN | OH | H | O | S |

TABLE 8-continued

| R¹ | R² | R³ 4- | R³ 6- | X | Y |
|---|---|---|---|---|---|
| biphenyl-4-yl | NO$_2$ | OH | H | O | S |
| biphenyl-4-yl | CN | OH | H | O | S |
| 4-hydroxyphenyl | NO$_2$ | OH | H | O | S |
| 4-hydroxyphenyl | CN | OH | H | O | S |
| 3-hydroxyphenyl | NO$_2$ | OH | H | O | S |
| 3-hydroxyphenyl | CN | OH | H | O | S |

TABLE 9

| R¹ | R² | R³ 4- | R³ 6- | X | Y |
|---|---|---|---|---|---|
| 2-hydroxyphenyl | NO$_2$ | OH | H | O | S |
| 2-hydroxyphenyl | CN | OH | H | O | S |
| furan-2-yl | NO$_2$ | OH | H | O | S |
| thiophen-2-yl | NO$_2$ | OH | H | O | S |
| 1H-pyrrol-2-yl | NO$_2$ | OH | H | O | S |

TABLE 9-continued

| R¹ | R² | R³ 4- | R³ 6- | X | Y |
|---|---|---|---|---|---|
| 1H-imidazol-4-yl | NO$_2$ | OH | H | O | S |
| thiazol-2-yl | NO$_2$ | OH | H | O | S |
| pyridin-2-yl | NO$_2$ | OH | H | O | S |
| pyridin-3-yl | NO$_2$ | OH | H | O | S |
| pyridin-4-yl | NO$_2$ | OH | H | O | S |

TABLE 10

| R¹ | R² | R³ 4- | R³ 6- | X | Y |
|---|---|---|---|---|---|
| 1H-indol-4-yl | NO$_2$ | OH | H | O | S |
| quinolin-8-yl | NO$_2$ | OH | H | O | S |

The pharmacological actions of the compound of the invention are described below.

The xanthine oxidase inhibiting action (in vitro test) of the compound of the invention was confirmed by measuring inhibition of oxidation of xanthine by xanthine oxidase, as described in Example 50. As is clear from Tables 11 and 12, the compounds of the invention show excellent xanthine oxidase inhibiting action.

The xanthine oxidase inhibiting action was. further confirmed in vivo tests by measuring the uric acid concentration in a plasma obtained from mouse into which the compound of the invention had been orally administered. See Example 51, Tables 11 and 12.

Accordingly, it is expected that the compounds of the invention having the formula (I) are employable for preventing or treating hyperuricemia and gout.

The compound of the invention can be administered into human beings by appropriate administration methods such as oral administration and parenteral administration.

The compounds of the invention can be prepared in the form of known pharmaceutical preparations such as pellets, granules, powders, capsules, suspensions, injections, and suppositories. For the preparations, a conventionally employed excipients, disintegrators, binder, lubricants, dyes, diluents, or the like are employed. The excipient may be lactose, D-mannitol, crystalline cellulose, or glucose. The disintegrator may be starch or carboxymethylcellulose calcium (CMC—Ca). The lubricant may be magnesium stearate or talc. The binder may be hydroxypropylcellulose (HPC), gelatin, or polyvinyl-pyrrolidone (PVP).

The dosage of the compound of the invention for adult generally is approximately 0.1 to 100 mg/day when it is administered in the form of an injection, and approximately 1 to 2,000 mg/day when it is orally administered. The dosage can be adjusted depending on age and clinical conditions.

The present invention is further described below by the following non-limiting examples and reference examples.

EXAMPLES

Reference Example 1

4-Chloro-N-(4-chloro-6-methoxy-5-pyrimidinyl)-3-nitrobenzamiae

4-Chloro-3-nitrobenzoic acid (30.2 g, 150 mmol) was suspended in ethyl acetate (150 mL), and thionyl chloride (22 mL, 300 mmol) was added to the resulting suspension. The suspension was then heated under refluxing for 5 hours. The reaction mixture was concentrated under reduced pressure. The residue was concentrated utilizing two portions of dry benzene and two portions of dichloromethane. The resulting acid chloride was dissolved in dichloromethane (20 mL), and the resulting solution was added to a solution of 5-amino-4-chloro-6-methoxypyrimidine (16.0 g, 100 mmol) in dichloromethane (100 mL). The resulting mixture was heated under refluxing for 16 hours. The heated mixture was then cooled to room temperature, and the precipitated crystalline product was collected by filtration and washed with four portions of dichloromethane (20 mL), to obtain 34.3 g (yield 100%) of the titled compound as a white crystalline product.

$^1$H-NMR (CDCl$_3$), δ: 4.07 (3H, s), 7.35 (1H, s), 7.74 (1H, d, J=8 Hz), 8.08 (1H, dd, J=2 Hz, 8 Hz), 8.42 (1H, d, J=2 Hz), 8.55 (1H, s).

Reference Example 2

2-(4-Chloro-3-nitrophenyl)-4-methoxythiazolo[5,4-d]pyrimidine

The above-mentioned 4-chloro-N-(4-chloro-6-methoxy-5-pyrimidinyl)-3-nitrobenzamide (150.6 g, 439 mmol) and Lawesson reagent (133.4 g, 130 mmol) were placed in THF (4.5 L). The mixture was heated under refluxing for 8 hours and then placed under reduced pressure to distill the solvent off. To the residue was added ethyl acetate (1.3 L), and the mixture was heated under refluxing for one-hour. To the mixture was then added hexane (1.3 L), and the resulting mixture was-cooled to room temperature. The precipitated crystalline product was collected by filtration, washed successively with a mixed solvent (700 mL) of ethyl acetate/hexane (1/2) and hexane (500 mL), and then subjected to silica gel column chromatography (chloroform). The obtained crystalline product was suspended in a mixed solvent (500 mL) of ethyl acetate/hexane (1/4). The suspension was heated under refluxing for 30 minutes and cooled to room temperature. The crystalline product was collected by filtration, washed with a mixed solvent (50 mL) of ethyl acetate/hexane (1/4), and dried under reduced pressure at room temperature, to obtain 33.3 g (yield 24%) of the titled compound as a pale yellow crystalline product.

m.p.: 235-238° C. (decomp.) $^1$H-NMR (CDCl$_3$, 400 MHz), δ: 4.28 (3H, s), 7.71 (1H, d, J=9 Hz), 8.22 (1H, dd, J=2 Hz, 9 Hz), 8.61 (1H, d, J=2 Hz), 8.72 (1H, s).

Reference Example 3

2-(4-Chloro-3-nitrophenyl)-4-hydroxythiazolo[5,4-d]pyrimidine

The above-mentioned 2-(4-chloro-3-nitrophenyl)-4-methoxythiazolo[5,4-d]pyrimidine (33.3 g, 103 maol) was suspended in dichloromethane (3 L), and to the suspension was dropwise added a solution of boron tribromide (39 mL, 413 mmol) in dichloromethane (330 mL). The mixture was stirred at room temperature for 46 hours, and then at a temperature of 37-38° C. for 13 hours. To the reaction mixture were successively added ice (600 g) and a saturated aqueous sodium hydrogen carbonate solution until the mixture reached pH 3-4. The mixture was then stirred for 30 minutes. The precipitated crystalline product was collected by filtration, washed successively with water (500 mL), dichloromethane (500 mL), water (500 mL), dichloromethane (500 mL), and acetone (200 mL), and dried in air. The crystalline product was suspended in ethyl acetate (160 mL), and the suspension was heated under refluxing for 30 minutes and then cooled to room temperature. The precipitated crystalline product was collected by filtration, washed with ethyl acetate (80 mL), and dried under reduced pressure at 50° C. to obtain 24.9 g (yield 78w) of the titled compound as a pale yellow crystalline product.

m.p.: 325-327° C. (decomp.) $^1$H-NMR (DMSO-d$_6$, 400 MHz), δ: 7.96 (1H, d, J=8 Hz), 8.2-8.4 (2H, m), 8.65 (1H, d, J=2 Hz), 12.95 (1H, s).

Reference Example 4

2-(4-Chloro-3-nitrophenyl)-4-mercaptothiazolo[5,4-d]pyrimidine

The 4-chloro-N-(4-chloro-6-methoxy-5-pyrimidinyl)-3-nitrobenzamide (100 mg, 0.29 mmol) and Lawesson reagent (80 mg, 0.20 mmol) were placed in toluene (2 mL). The mixture was heated under refluxing for 5 hours and placed under reduced pressure to distill the solvent off. The residue was purified by silica gel column chromatography (ethyl acetate/hexane), to obtain 10.2 mg (yield 11%) of the titled compound as a yellow crystalline product.

$^1$H-NMR (CD$_3$OD/CDCl$_3$(1/20), 400 MHz), δ: 7.71 (1H, d, J=8 Hz), 8.05 (1H, s), 8.28 (1H, dd, J=2 Hz, 8 Hz), 8.32 (1H, s), 8.58 (1H, d, J=2 Hz).

Example 1

2-[4-(4-Chlorophenylthio)-3-nitrophenyl]-4-mercaptothiazolo[5,4-d]pyrimidine The above-mentioned 2-(4-chloro-3-nitrophenyl)-4-mercaptothiazolo[5,4-d]pyrimidine (10.2 mg, 0.031 mmol), potassium carbonate (6.1 mg, 0.044 nmol) and 4-chlorothiophenol (47 mg, 0.032 mmol) were added to ethanol (2 mL). The resulting mixture was heated under refluxing for 2 hours, and then placed under reduced pressure to distill the solvent off. To the residue were added water (0.5 mL) and then 1M aqueous hydrochloric acid until the aqueous mixture reached pH 2. The resulting mixture was subjected to extraction with ethyl acetate. The extract was dried over anhydrous sodium sulfate and placed under reduced pressure to distill the solvent off. The residue was purified by silica gel column chromatography (ethyl acetate/hexane), to obtain 8.9 mg (yield 66%) of the titled compound as a yellow crystalline product.

$^1$H-NMR (CD$_3$OD/CDCl$_3$=1/20, 400 MHz), δ: 7.07 (1H, d, J=9 Hz), 7.6-7.8 (4H, m), 8.17 (1H, dd, J=2 Hz, 9 Hz), 8.32 (1H, s), 8.81 (1H, dd, J=2 Hz, 9 Hz), 14.31 (1H, s).

FAB-MS (m/e): 433 (M+1).

Example 2

2-[4-(4-Chlorophenylthio)-3-nitrophenyl]-4-hydroxythiazolo[5,4-d]pyrimidine

The aforementioned 2-(4-chloro-3-nitrophenyl)-4-hydroxythiazolo[5,4-d]pyrimidine (123 mg, 0.40 mmol), potassium carbonate (77 mg, 0.56 mmol), 4-chlorothiophenol (64 mg, 0.44 mmol), and ethanol (22 mL) were mixed, and the mixture was heated under refluxing for 3 hours in a nitrogen atmosphere. To mixture was then added 2M hydrochloric acid (1 mL) under stirring with ice-cooling, and the resulting mixture was stirred at room temperature for 30 minutes. The precipitated crystalline product was collected.by filtration, washed successively with two portions of ethanol and three portions of water, to obtain 32 mg (yield 79%) of the titled compound as a yellow crystalline product.

$^1$H-NMR (DMSO-d$_6$), δ: 7.06 (1H, d, J=8 Hz), 7.66 (2H, d, J=7 Hz), 7.71 (2H, d, J=7 Hz), 8.16 (1H, d, J=8 Hz), 8.26 (1H, s), 8.77 (1H, s), 12.95 (1H, s).

FAB-MS (m/e): 417 (M+1).

Example 3

2-[4-(4-Chlorophenylthio)-3-nitrophenyl]-4-hydroxythiazolo[5,4-d]pyrimidine potassium salt The above-mentioned 2-[4-(4-chlorophenylthio)-3-nitrophenyl]-4-hydroxythiazolo[5,4-d]pyrimidine (42 mg, 0.10 mmol) was dissolved in a mixture of chloroform (21 mL) and methanol (7 mL). After addition of a solution of 86% potassium hydroxide (7 mg, 0.11 mmol) in methanol (3.5 mL), the mixture was concentrated under reduced pressure. The residue was successively washed with methanol and chloroform, to obtain 24 mg (yield 53%) of the titled compound as a yellow crystalline product.

$^1$H-NMR (DMSO-d$_6$), δ: 7.03 (1H, d, J=8 Hz), 7.64 (2H, d, J=9 Hz), 7.70 (2H, d, J=9 Hz), 7.96 (1H, s), 8.05 (1H, dd, J=2 Hz, 8 Hz), 8.69 (1H, d, J=2 Hz).

Example 4

4-Hydroxy-2-(3-nitro-4-phenylthiophenyl)thiazolo[5,4-d]pyrimidine

The aforementioned 2-(4-chloro-3-nitrophenyl)-4-hydroxythiazolo[5,4-d]pyrimidine (15 mg, 0.049 mmol), potassium carbonate (10 mg, 0.072 mmol), and a solution of 1% thiophenol in ethanol (0.7 mL, 0.064 mmol) were added to ethanol (2 mL), and the mixture was heated over-night under refluxing. After addition of potassium carbonate (10 mg, 0.072 mmol) and a solution of 1% thiophenol in ethanol (0.7 mL, 0.064 mmol), the mixture was heated under refluxing for 5 hours, and cooled to room temperature. To the reaction mixture were added water (3.4 mL) and 1M aqueous hydrochloric acid until the mixture reached pH 6-7. The precipitated crystalline product was collected by filtration, washed successively with a mixture (1 mL) of ethanol and water (1/1) and water (0.5 mL), and dried at room temperature under reduced pressure, to obtain 12.8 g (yield 68%) of the titled compound as a yellow crystalline product.

$^1$H-NMR (DMSO-d$_6$, 400 MHz) δ: 7.01 (1H, d, J=9 Hz), 7.5-7.6 (3H, m), 7.6-7.8 (2H, m), 8.15 (1H, dd, J=2 Hz, 9 Hz), 8.26 (1H, s), 8.78 (1H, d, J=2 Hz), 12.94 (1H, s).

FAB-MS (m/e): 383 (M+1).

Example 5

2-[4-(4-Chlorophenoxy)-3-nitrophenyl]-4-hydroxythiazolo[5,4-d]pyrimidine

To a solution of 4-chlorophenol (1.80 g, 14.0 mmol) in DMSO (36 mL) was added 60% sodium hydride (1.17 g, 29.3 mmol) under ice-cooling, and the mixture was stirred at room temperature for 30 minutes. After addition of the aforementioned 2-(4-chloro-3-nitrophenyl)-4-hydroxy-thiazolo[5,4-d]pyrimidine (3.60 g, 11.7 mmol), the mixture was stirred at room temperature for 24 hours. To the mixture was added ice-water (36 mL) and 1M aqueous hydrochloric acid until the mixture reached pH 4. The precipitated crystalline product was collected by filtration and washed with water (50 mL×2). The obtained crystalline product was suspended in a mixture (30 mL) of ethanol and water (1/1), and the suspension was stirred at room temperature for 30 minutes. The precipitated crystalline product was collected, washed successively with a mixture (20 mL) of ethanol and water (1/1) and water (50 mL), and dried at room temperature under reduced pressure. The dry product was then purified repeatedly by silica gel column chromatography (methanol/chloroform). The obtained crystalline product was suspended in ethanol (140 mL), and the suspension was heated under refluxing for 10 minutes and then cooled to room temperature. The crystalline product was collected by filtration, washed with ethanol (20 mL), and dried at room temperature under reduced pressure, to obtain 2.65 g (yield 57w) of the titled compound as a yellow crystalline product.

m.p.: 304-306° C. (decomp.)

$^1$H-NMR (DMSO-d$_6$, 400 MHz), δ: 7.22-7.27 (2H, m), 7.29 (1H, d, J=9 Hz), 7.5-7.6 (2H, m), 8.2-8.3 (2H, m), 8.64 (1H, d, J=2 Hz), 12.94 (1H, s).

IR (KBr) cm$^{-1}$: 3066, 2924, 2345, 1695, 1616, 1570, 1537, 1481, 1456, 1419, 1352, 1304, 1265, 1248, 1223, 1196, 1159, 1151, 1128, 1084, 1014, 978, 850.

FAB-MS (m/e): 401 (M+1).

Reference Example 5

Ethyl 4-(4-chlorophenylthio)-3-nitrobenzoate

In ethanol (15 mL) were suspended ethyl 4-chloro-3-nitrobenzoate (1.10 g, 4.79 mmol), 4-chlorothiophenol (0.72 g, 4.98 mmol) and potassium carbonate (0.95 g, 6.78 mmol), and the suspension was heated under refluxing for 3 hours. The mixture was then placed under reduced pressure to distill the solvent off. After addition of water (100 mL), the mixture was subjected to extraction with ethyl acetate (100 mL×2) and dried over anhydrous sodium sulfate. The dry extract was placed under reduced pressure to distill the solvent off. The residue was purified-by silica gel column chromatography (ethyl acetate/hexane), to obtain 767 mg (yield 47%) of the titled compound as a yellow crystalline product.

$^1$H-NMR (CDCl$_3$, 400 MHz), δ: 1.40 (3H, t, J=7 Hz), 4.40 (2H, q, J=7 Hz), 6.90 (1H, d, J=9 Hz), 7.4-7.6 (4H, m), 7.97 (1H, dd, J=2 Hz, 9 Hz), 8.86 (1H, d, J=2 Hz).

Reference Example 6

4-(4-Chlorophenylthio)-3-nitro-benzoic acid

The above-mentioned ethyl 4-(4-chlorophenylthio)-3-nitrobenzoate (760 mg, 2.25 mmol) was dissolved in a mixture of ethanol (5 mL) and THF (10 mL). After addition of 2M aqueous sodium hydroxide (2.25 mL, 4.50 mmol), the mixture was stirred at room temperature for 4 hours and placed under reduced pressure to distill the solvent off. To the residue were added water (20 mL) and 2M aqueous hydrochloric acid until the mixture reached pH 2. The precipitated crystalline product was collected by filtration, washed successively with water (5 mL×3), a mixture (5 mL) of ethanol and water (1/4) and hexane (5 mL×2), and dried at 40° C. under reduced pressure, to obtain 703 mg (yield 100%) of the titled compound as a yellow crystalline product.

$^1$H-NMR (CDCl$_3$, 400 MHz): 6.85 (1H, d, J=9 Hz), 7.4-7.6 (4H, m), 7.96 (1H, dd, J=2 Hz, 9 Hz), 8.82 (1H, d, J=2 Hz).

Reference Example 7

4-(4-Chlorophenylthio)-3-nitro-benzoic anhydride

The above-mentioned 4-(4-chlorophenylthio)-3-nitrobenzoic acid (260 mg, 0.84 mmol) was suspended in thionyl chloride (2 mL). After addition of DMF (one drop), the suspension was heated under refluxing for 1.5 hours, and placed under reduced pressure to distill the solvent off. The residue was added to dry benzene, and the mixture was placed under reduced pressure to distill the dry benzene with the remaining thionyl chloride off. The residue was dissolved in dry THF (7 mL). To the solution were added under ice-cooling 4-(4-chlorophenylthio)-3-nitrobenzoic acid (260 mg, 0.84 mmol) and triethylamine (0.5 mL, 3.59 mmol). The resulting mixture was heated under refluxing for 18 hours, cooled to room temperature, and placed under reduced pressure to distill the solvent off. The residue was dissolved in chloroform (50 mL). The solution was washed with 0.5M aqueous hydrochloric acid (10 mL), saturated aqueous sodium hydrogen carbonate (10 mL) and saturated aqueous sodium chloride (10 mL), dried over anhydrous sodium sulfate, and placed under reduced pressure to distill the solvent off, to obtain 417 mg (83%) of the titled compound as a brown crystalline product.

$^1$H-NMR (CDCl$_3$, 400 MHz), δ: 6.99 (2H, d, J=9 Hz), 7.4-7.6 (8H, m), 8.02 (2H, dd, J=2 Hz, 9 Hz), 8.92 (2H, d, J=2 Hz).

Example 6

2-[4-(4-Chlorophenylthio)-3-nitrophenyl]-4-hydroxyoxazolo[5,4-d]pyrimidine

The above-mentioned 4-(4-chlorophenylthio)-3-nitrobenzoic anhydride (300 mL, 0.50 mmol) and 5-amino-4,6-dihydroxypyrimidine hydrochloride (50 mg, 0.31 mmol) were heated under stirring at 150° C. for one hour, and then cooled to room temperature. The resulting residue was purified by silica gel column chromatography (methanol/chloroform). The obtained crude product was then stirred in chloroform (10 mL) for 30 minutes. The resulting crystalline product was collected by filtration and washed with chloroform, to obtain 21 mg (yield 13%) of the titled compound as a yellow crystalline product.

m.p.: >250° C.

$^1$H-NMR (DMSO-d$_6$, 400 MHz), δ: 7.10 (1H, d, J=9 Hz), 7.67 (2H, d, J=8 Hz), 7.71 (2H, d, J=8 Hz), 8.22 (1H, dd, J=2 Hz, 9 Hz), 8.30 (1H, s), 8.79 (1H, d, J=2 Hz), 13.04 (1H, s).

IR (KBr) cm$^{-1}$: 3429, 3076, 1720, 1612, 1549, 1522, 1475, 1458, 1338, 1298, 1240, 1207, 1093, 1066, 1014, 906, 876, 825, 781, 748, 729.

FAB-MS (m/e): 401 (M+1).

Example 7

4-Hydroxy-2-(3-nitro-4-phenoxyphenyl)-thiazolo[5,4-d]pyrimidine

To a suspension of 60% sodium hydride (360 mg, 9.00 mmol) in DMSO (12 mL) was added under water-cooling phenol (847 mg, 9.00 mmol). The mixture was stirred at room temperature and then at 50° C. for one hour. After addition of the aforementioned 2-(4-chloro-3-nitrophenyl)-4-hydroxythiazolo[5,4-d]pyrimidine (926 mg, 3.00 mmol), the mixture was stirred at room temperature for 6 hours. To the reaction mixture were added under stirring and water-cooling 2M hydrochloric acid (6 mL) and water (18 mL), and the mixture was stirred for 30 minutes. The precipitated crystalline product was collected by filtration, washed with several portions of water, dried overnight in air, and again washed successively with three portions of ether (3 mL), three portions of chloroform (6 mL) and two portions of ethanol (9 mL), to obtain 880 mg (yield 80%) of the titled compound as a yellow crystalline product.

m.p.: 278-281° C. (decomp.)

$^1$H-NMR (DMSO-d$_6$), δ: 7.2-7.6 (6H, m), 8.25 (1H, s), 8.26 (1H, dd, J=2 Hz, 8 Hz), 8.63 (1H, d, J=2 Hz), 12.93 (1H, s).

IR (KBr) cm$^{-1}$: 3070, 1697, 1616, 1589, 1570, 1537, 1489, 1456, 1350, 1304, 1265, 1246, 1221, 1192, 1161, 760.

FAB-MS (m/e): 367 (M+1).

Example 8

2-(3-Nitro-4-phenoxyphenyl)-4-hydroxythia-zolo[5,4-d]pyrimidine potassium salt

The aforementioned 2-(3-nitro-4-phenoxyphenyl)-4-hydroxythiazoto[5,4-d]pyrimidine (250 mg, 0.68 mmol) was suspended in ethanol (10 mL). After addition of ethanol solution (1.36 mL, 0.68 mol) containing 0.5 mol/L potassium hydroxide, the suspension was stirred at room temperature for 3 hours. The precipitated solid product was collected by filtration, washed with ethanol, and dried at room temperature under reduced pressure, to obtain 227 mg (yield 82%) of the titled compound as a yellow crystalline product.

m.p.: >260° C. (decomp.)

$^1$H-NMR (DMSO-d$_6$, 400 MHz), δ: 7.2-7.3 (4H, m), 7.4-7.5 (2H, m), 7.95 (1H, s), 8.15 (1H, dd, J=2 Hz, 9 Hz), 8.52 (1H, d, J=2 Hz).

IR (KBr) cm$^{-1}$: 3421, 1618, 1577, 1573, 1481, 1338, 1294, 1261, 1192, 1163, 1081, 1022, 985, 898, 843, 804, 750, 690.
FAB-MS (m/e): 405 (M+1).

Reference Example 8

4-Chloro-3-cyanobenzoic acid

To a stirred mixture of conc. sulfuric acid (60 mL) and water (95 mL) containing 3-amino-4-chlorobenzoic acid (10.0 g, 57.1 mmol) was added sodium nitrite (10.0 g, 145 mmol) at 0° C. The mixture was stirred at 0° C. for 2 hours, and added to a stirred mixture comprising a mixture of water (250 mL) and benzene (175 mL) containing copper cyanide (7.1 g, 79.3 mmol), potassium cyanide (21.7 g, 333 mmol), potassium carbonate (285 g, 2.06 mmol) at a temperature not higher than 15° C. The resulting mixture was heated under stirring at 80° C. for one hour, cooled to room temperature, stirred under ice-cooling, and filtered using Celite to collect insolubles. The insolubles were washed with benzene (100 mL) and ether (100 mL). The aqueous portion was taken out, and made to pH 2 by addition of conc. hydrochloric acid under stirring and ice-cooling. The aqueous portion was subjected to extraction with ether (200 mL×2), dried over anhydrous sodium sulfate, and placed under reduced pressure to distill the solvent off. The residue was repeatedly purified by silica gel column chromatography (ethyl acetate/hexane), to obtain 2.0 g (yield 19%) of the titled compound as a pale yellow crystalline product.

$^1$H-NMR (CDCl$_3$/CD$_3$OD/=20/1, 400 MHz), δ: 7.61 (1H, d, J=9 Hz), 8.20 (1H, dd, J=2 Hz, 9 Hz), 8.36 (1H, d, J=2 Hz).

Reference Example 9

4-Chloro-N-(4-chloro-6-methoxy-5-pyrimidinyl)-3-cyanobenzamide

To a suspension of the above-mentioned 4-chloro-3-cyanobenzoic acid (1.20 g, 6.61 mmol) in dry benzene (10 mL) was added thionyl chloride (0.58 mL, 7.95 mmol). The mixture was heated under refluxing for 4 hours, and then placed under reduced pressure to distill the solvent off. To the residue was added dry dichloromethane (5 mL), and the mixture was placed under reduced pressure to distill the dry benzene and the remaining thionyl chloride off. The residue was dissolved in dry dichloromethane (45 mL). The resulting solution was dropwise added under ice-cooling to a solution of 5-amino-4-chloro-6-methoxypyrimidine (2.11 g, 13.2 mmol) in dry dichloromethane (45 mL) for 5 minutes. The mixture was stirred at room temperature for 115 hours. The precipitated crystalline product was collected by filtration, washed with dichloromethane (5 mL×2), and placed under reduced pressure to distill the solvent off. The residue was repeatedly purified by silica gel column chromatography (methanol/chloroform), to obtain 1.61 g (yield 75%) of the titled compound as a pale brown crystalline product.

$^1$H-NMP (CDCl$_3$, 400 MHz), δ: 4.07 (3H, s), 7.40 (1H, s), 7.69 (1H, d, J=9 Hz), 8.09 (1H, dd, J=2 Hz, 9 Hz), 8.23 (1H, d, J=2 Hz), 8.54 (1H, s).

Reference Example 10

2-(4-Chloro-3-cyanophenyl)-4-methoxythiazolo[5,4-d]pyrimidine

In a nitrogen atmosphere, the above-mentioned 4-chloro-N-(4-chloro-6-methoxy-5-pyrimidinyl)-3-cyanobenz-amide (1.10 g, 3.40 mmol) and Lawesson reagent (1.03 g, 2.55 mmol) were suspended in dry benzene (40 mL) and the suspension was heated under refluxing for 16 hours. The suspension was then placed under reduced pressure to distill the solvent off. The residue was purified by silica gel column chromatography to obtain 403 mg (yield 39%) of the titled compound as a white crystalline product.

$^1$H-NMR (CDCl$_3$, 400 MHz), δ: 4.28 (3H, s), 7.67 (1H, d, J=9 Hz), 8.22 (1H, dd, J=2 Hz, 9 Hz), 8.44 (1H, d, J=2 Hz), 8.72 (1H, s).

Reference Example 11

2-(4-Chloro-3-cyanophenyl)-4-hydroxythiazolo[5,4-d]pyrimidine

In a nitrogen atmosphere, the above-mentioned 2-(4-chloro-3-cyanophenyl)-4-methoxythiazolo[5,4-d]pyrimidine (164 mg, 0.54 mmol) was suspended in dry dichloromethane (15 mL). After addition of a solution of boron tribromide (0.3 mL, 3.17 mmol) in dry dichloromethane (15 mL), the mixture was stirred at room temperature for 16 hours. After addition of a solution of boron tribromide (0.05 mL, 0.53 mmol) in dry dichloromethane (2.5 mL), the mixture was stirred at room temperature for 24 hours. To the mixture was further added a solution of boron tribromide (0.1 mL, 1.06 mmol) in dry dichloromethane (5 mL). The resulting mixture was stirred at room temperature for 96 hours, and placed under reduced pressure to distill the solvent off. To the residue was added ice-water (20 mL). The precipitated crystalline product was collected by filtration and washed with water (5 mL×3). Thus obtained crude crystalline product was suspended in ethanol (20 mL). The suspension was then placed under reduced pressure to distill the solvent off. To the residue was added chloroform (20 mL) and the mixture was stirred at room temperature for 20 minutes. The precipitated crystalline product was collected by filtration and washed with chloroform (5 mL×3), to obtain 149 mg (yield 96%) of the titled compound as a pale brown crystalline product.

$^1$H-NMR (DMSO-d$_6$, 400 MHz), δ: 7.94 (1H, d, J=8 Hz), 8.27 (1H, d, J=4 Hz), 8.35 (1H, dd, J=2 Hz, 8 Hz), 8.57 (1H, d, J=2 Hz), 12.94 (1H, s).

IR (KBr) cm$^{-1}$: 3427, 3028, 2933, 2233, 1714, 1676, 1601, 1585, 1570, 1491, 1489, 1466, 1392, 1356, 1286, 1252, 1174, 1138, 1059, 1024, 978, 903, 893, 856, 806.

Example 9

2-[4-(4-Chlorophenylthio)-3-cyanophenyl]-4-hydroxythiazolo[5,4-d]pyrimidine

In a nitrogen atmosphere, the above-mentioned 2-(4-chloro-3-cyanophenyl)-4-hydroxythiazolo[5,4-d]pyrimidine (60 mg, 0.21 mmol), 4-chlorothiophenol (34 mg, 0.24 mmol) and potassium carbonate (41 mg, 0.30 mmol) were suspended in dry ethanol (15 mL), and the suspension was heated under refluxing for 5 hours. To the suspension were further added 4-chlorothiophenol (34 mg, 0.24 mmol), potassium carbonate (41 mg, 0.03 mmol) and dry ethanol (15 mL), and the resulting mixture was heated under refluxing for 3 hours. To-the mixture were furthermore added 4-chlorothiophenol (34 mg, 0.24 mmol) and potassium carbonate (41 mg, 0.30 mmol). The mixture was then heated under refluxing for 3 hours, and cooled to room temperature. To the cooled mixture was added under ice-cooling 1M aqueous hydrochloric acid until the mixture reached pH 3. The precipitated crystalline product was collected by filtration, washed with ethanol (5 mL×2) and water (5 mL×3), and dried at 50° C. under reduced pressure, to obtain 60 mg (yield 75%) of the titled compound as a pale brown crystalline product.

$^1$H-NMR (DMSO-$d_6$, 400 MHz), δ: 7.31 (1H, d, J=9 Hz), 7.59 (4H, s), 8.21 (1H, dd, J=2 Hz, 9 Hz), 8.25 (1H, s), 8.48 (1H, d, J=2 Hz), 12.92 (1H, s).

IR (KBr) cm$^{-1}$: 3433, 1680, 1597, 1572, 1477, 1462, 1383, 1356, 1248, 1178, 1092, 1059, 1012, 974, 912, 891, 820, 746, 708.

FAB-MS (m/e): 397 (M+1)

Example 10

2-[4-(4-Chlorophenylthio)-3-cyanophenyl]-4-hydroxythiazolo[5,4-d]pyrimidine potassium salt The above-mentioned 2-[4-(4-chlorophenylthio)-3-cyanophenyl]-4-hydroxythiazolo[5,4-d]pyrimidine (120 mg, 0.30 mmol) was suspended in ethanol (6 mL). After addition of 0.5 mol/L potassium hydroxide in ethanol (0.7 mL), the suspension was stirred at room temperature for one hour. The precipitated crystalline product was collected by filtration, washed with ethanol (5 mL), and dried at 50° C. under reduced pressure, to obtain 126 mg (yield 97%) of the titled compound as a yellow crystalline product.

m.p.: 290-295° C. (decomp.)

$^1$H-NMR (DMSO-$d_6$, 400 MHz), δ: 7.36 (1H, d, J=8 Hz), 7.5-7.6 (4H, m), 7.96 (1H, s), 8.13 (1H, dd, J=2 Hz, 8 Hz), 8.35 (1H, d, J=2 Hz).

IR (KBr) cm$^{-1}$: 3421, 3394, 2225, 1576, 1468, 1396, 1389, 1329, 1298, 1211, 1136, 1093, 1065, 1011, 984.

FAB-MS (m/e): 435 (M+1)

Example 11

2-[4-(4-Chloro-1-naphthoxy)-3-nitrophenyl]-4-hydroxythiazolo[5,4-d]pyrimidine

To a suspension of 60% sodium hydride (20 mg, 0.50 mmol) in DMSO (3 mL) was added 4-chloro-1-naphthol (71 mg, 0.40 mmol). The mixture was stirred at room temperature for 30 minutes. To the resulting dark green solution was added the aforementioned 2-(4-chloro-3-nitro-phenyl)-4-hydroxythiazolo[5,4-d]pyrimidine (31 mg, 0.10 mmol). The mixture was stirred at room temperature for 30 minutes, at 50° C. for 16 hours, and then at 60° C. for 24 hours. To the reaction mixture were added under ice-cooling cooled water (2.5 mL) and 2M hydrochloric acid (0.5 mL). The mixture was stirred for 10 minutes. The precipitated crystalline product was collected by filtration, washed successively with water and ethanol, and subjected to extraction with chloroform. The chloroform extract was concentrated under reduced pressure to give 55 mg of a brown solid product. The brown solid product was processed by silica gel column chromatography and eluted with a mixture of hexane and ethyl acetate (1/2), to obtain 14 mg (yield 31o) of the titled compound as a brown crystalline product.

$^1$H-NMR (CDCl$_3$), δ: 6.95 (1H, d, J=9 Hz), 7.10 (1H, d, J=8 Hz), 7.59 (1H, d, J=9 Hz), 7.6-7.8 (2H, m), 8.1-8.2 (2H, m), 8.14 (1H, s), 8.34 (1H, d, J=8 Hz), 8.71 (1H, d, J=2 Hz), 11.68 (1H, s).

FAB-MS (m/e): 451 (M+1)

Example 12

2-[4-(4-Fluorophenoxy)-3-nitrophenyl]-4-hydroxythiazolo[5,4-d]pyrimidine

In a nitrogen atmosphere, 4-fluorophenol (1.09 g, 9.72 mmol) was dissolved in DMSO (25 mL), and to the solution was added under ice-cooling 60% sodium hydride (810 mg, 20.3 mmol). The resulting mixture was stirred at room temperature for 30 minutes. To the mixture was added under ice-cooling the aforementioned 2-(4-chloro-3-nitrophenyl)-4-hydroxythiazolo[5,4-d]pyriimidine (2.50 g, 8.10 mmol). The mixture was then stirred at room temperature for 24 hours. To the mixture were added ice-water (75 mL) and 1M aqueous hydrochloric acid until the mixture reached pH 4. The precipitated crystalline product was collected by filtration and washed with water (25 ML×2). Thus obtained crude crystalline product was suspended in ethanol/water (1/1, 75 mL), and the suspension was stirred at room temperature for 30 minutes. The precipitated crystalline product was collected by filtration, dried under reduced pressure, and then purified by silica gel column chromatography (methanol/chloroform) and by repeated washing with a mixture of methanol and chloroform. The obtained crystalline product was suspended in ethanol (93 mL), stirred at room temperature for 6 hours, collected by filtration, washed with ethanol (20 mL×2), and dried at 40° C. under reduced pressure, to obtain 2.03 g (yield 59%) of the titled compound as a yellow crystalline product.

m.p.: 282-284° C. (decomp.)

$^1$H-NMR (DMSO-$d_6$, 400 MHz), δ: 7.19 (1H, d, J=9 Hz), 7.2-7.4 (4H, m), 8.25 (1H, dd, J=2 Hz, 9 Hz), 8.26 (1H, s), 8.62 (1H, d, J=2 Hz), 12.92 (1H, s).

IR (KBr) cm$^{-1}$: 2798, 2345, 1682, 1618, 1574, 1535, 1500, 1470, 1354, 1265, 1223, 1184, 1084, 1014, 970, 908, 839, 837, 816, 766, 708.

FAB-MS (m/e): 385 (M+1)

Example 13

2-[4-(4-Fluorophenoxy)-3-nitrophenyl]-4-hydroxythiazolo[5,4-d]pyrimidine potassium salt The above-mentioned 2-[4-(4-fluorophenoxy)-3-nitrophenyl]-4-hydroxythiazolo[5,4-d]pyrimidine (250 mg, 0.65 mmol) was suspended in ethanol (10 mL). After addition of 0.5 mol/L potassium hydroxide in ethanol (1.3 mL, 0.65 mmol), the suspension was stirred at room temperature for 2.5 hours. The precipitated solid product was collected by filtration, washed with ethanol, and dried at room temperature under reduced pressure, to obtain 257 mg (yield 94%) of the titled compound as a yellow crystalline product.

m.p.: >260° C. (decomp.)

$^1$H-NMR (DMSO-$d_6$, 400 MHz), δ: 7.16 (1H, d, J=9 Hz), 7.3-7.4 (4H, m), 7.95 (1H, s), 8.13 (1H, dd, J=2 Hz, 9 Hz), 8.51 (1H, d, J=2 Hz).

IR (KBr) cm$^{-1}$: 3398, 1620, 1570, 1537, 1500, 1479, 1340, 1294, 1267, 1227, 1221, 1184, 899, 850, 818, 816, 764, 760.

FAB-MS (m/e): 423 (M+1)

Example 14

2-[4-(4-Methoxyphenoxy)-3-nitrophenyl]-4-hydroxythiazolo[5,4-d]pyrimidine

To a solution of 4-methoxyphenol (19 mg, 0.15 mmol) in DMSO (2 mL) was added 60% sodium hydride (10 mg, 0.25 mmol) under ice-cooling. The mixture was stirred at room temperature for 30 minutes. To the mixture was then added the aforementioned 2-(4-chloro-3-nitrophenyl)-4-hydroxythiazolo[5,4-d]pyrimidine (40 mg, 0.13 mmol). The resulting mixture was stirred at room temperature for 21 hours. After addition of 4-methoxyphenol (10 mg, 0.081 mmol) and 60% sodium hydride (5 mg, 0.13 mmol), the mixture was further stirred at room temperature for 18 hours. To the mixture were added ice-water (5 mL) and 1M aqueous hydrochloric acid until the mixture reached pH 4. The precipitated crystalline product was collected by filtration, washed successively with water (5 mL) and ether (5 mL), and dried at room temperature under reduced pressure. Thus obtained crystalline product was purified by silica gel column chromatography (methanol/chloroform), to obtain 18.8 mg (yield 37%) of the titled compound as a yellow crystalline product.

$^1$H-NMR (CD$_3$OD/CDCl$_3$=1/10, 400 MHz), δ: 3.85 (3H, s), 6.9-7.0 (2H, m), 7.01 (1H, d, J=9 Hz), 7.06-7.11 (2H, m), 8.03 (1H, s), 8.15 (1H, dd, J=2 Hz, 9 Hz), 8.60 (1H, d, J=2 Hz).

FAB-MS (m/e): 397 (M+1).

Example 15

2-[4-(4-Methoxyphenoxy)-3-nitrophenyl]-4-hydroxythiazolo[5,4-d]pyrimidine potassium salt The above-mentioned 2-[4-(4-methoxyphenoxy)-3-nitrophenyl]-4-hydroxythiazolo[5,4-d]pyrimidine (700 mg, 1.77 mmol) was suspended in ethanol (40 mL). After addition of 0.5 mol/L potassium hydroxide in ethanol (3.53 mL, 1.77 mmol), the suspension was stirred overnight at room temperature. The precipitated solid product was collected by filtration, washed with ethanol, and dried at room temperature under reduced pressure, to obtain 730 mg (yield 95%) of the titled compound as a yellow crystalline product.

m.p.: >260° C. (decomp.)

$^1$H-NMR (DMSO-d$_6$, 400 MHz), δ: 3.78 (3H, s), 7.04 (2H, dd, J=2 Hz, 7 Hz), 7.05 (1H, d, J=9 Hz), 7.17 (2H, dd, J=2 Hz, 7 Hz), 7.93 (1H, s), 8.10 (1H, dd, J=2 Hz, 9 Hz), 8.47 (1H, d, J=2 Hz).

IR (KBr) cm$^{-1}$: 1620, 1571, 1535, 1502, 1481, 1344, 1342, 1295, 1240, 1191, 1034, 829, 827, 804.

FAB-MS (m/e): 435 (M+1).

Example 16

4-Hydroxy-2-[3-nitro-4-[4-(trifluoromethyl)-phenoxy]phenyl]thiazolo[5,4-d]pyrimidine To a suspension of 60% sodium hydride (20 mg, 0.50 mmol) in DMSO (3 mL) was added 4-(trifluoromethyl)phenol (65 mg, 0.40 mmol), and the mixture was stirred at room temperature for one hour. After addition of the aforementioned 2-(4-chloro-3-nitrophenyl)-4-hydroxythiazolo-[5,4-d]pyrimidine (31 mg, 0.10 mmol), and the mixture was stirred at 50° C. for 41 hours. To the reaction mixture were added cooled water (2.5 mL) and 2M hydrochloric acid (0.5 mL) under ice-cooling and stirring, and the mixture was stirred for 30 minutes. The precipitated crystalline product was collected by filtration, washed successively with water, ethanol, chloroform, ether and hexane, to obtain 3 mg (yield 7%) of the titled compound as a yellow crystalline product).

$^1$H-NMR (DMSO-d$_6$), δ: 7.37 (2H, d, J=9 Hz), 7.47 (1H, d, J=9 Hz), 7.83 (2H, d, J=9 Hz), 8.27 (1H, s), 8.33 (1H, dd, J=2 Hz, 9 Hz), 8.70 (1H, d, J=2 Hz), 12.95 (1H, s).

FAB-MS (m/e): 435 (M+1)

Example 17

2-[4-(3-Chlorophenoxy)-3-nitrophenyl]-4-hydroxythiazolo[5,4-d]pyrimidine

To a solution of 3-chlorophenol (20 mg, 0.16 mmol) in DMSO (2 mL) was added 60% sodium hydride (10 mg, 0.25 mmol) under ice-cooling. The mixture was stirred at room temperature for 30 minutes. After addition of the aforementioned 2-(4-chloro-3-nitrophenyl)-4-hydroxythiazolo-[5,4-d]pyrimidine(40 mg, 0.13 mmol), the mixture was stirred at room temperature for 21 hours. After addition of 3-chlorophenol (10 mg, 0.081 mmol) and 60% sodium hydride (5 mg, 0.13 mmol), the mixture was further stirred at room temperature for 17 hours. To the mixture were added ice-water (5 mL) and 1M aqueous hydrochloric acid, until the mixture reached pH 4. Thus precipitated crystalline product was collected by filtration, washed successively with water (5 mL) and ether (5 mL), and dried at room temperature under reduced pressure. The crystalline product was purified by silica gel column chromatography (methanol/chloroform), to obtain 10.1 mg (yield 19%) of the titled compound as a pale orange amorphous product.

$^1$H-NMR (CDCl$_3$, 400 MHz), δ: 7.0-7.1 (1H, m), 7.1-7.2 (1H, m), 7.14 (1H, d, J=9 Hz), 7.2-7.3 (1H, m), 7.37 (1H, t, J=8 Hz), 8.11 (1H, s), 8.23 (1H, dd, J=2 Hz, 9 Hz), 8.64 (1H, d, J=2 Hz).

FAB-MS (m/e): 401 (M+1).

Example 18

2-[4-(2-Chlorophenoxy)-3-nitrophenyl]-4-hydroxythiazolo[5,4-d]pyrimidine

To a suspension of 60% sodium hydride (1.54 g, 38.5 mmol) in DMSO (60 mL) was added 2-chlorophenol (2.97 g, 23.1 mmol) under ice-cooling for 5 minutes. The mixture was stirred under ice-cooling for 30 minutes, and then at room temperature for one hour. After addition of the aforementioned 2-(4-chloro-3-nitrophenyl)-4-hydroxy-thiazolo[5,4-d]pyrimidine (4.75 g, 15.4 mmol) under ice-cooling for 5 minutes, the mixture was stirred under ice-cooling for 2 hours, and then at room temperature for 25 hours. After addition of cooled water (60 mL) under ice-cooling and stirring, the reaction mixture was stirred for 30 minutes. To the mixture was dropwise added 2M hydrochloric acid (20 mL) under ice-cooling and stirring for 5 minutes, and the mixture was stirred under ice-cooling for one hour. The precipitated crystalline product was collected by filtration, washed with five portions of water (40 mL), two portions of ether (20 mL) and two portions of hexane (20 mL), to obtain 5.6 g of a yellow crystalline product. The crystalline product was processed by silica gel column chromatography and eluted with a mixture of methanol and chloroform (1/20-1/5), to obtain 5.2 g of a yellow crystalline product. Thus obtained crystalline product was suspended in a mixture (52 mL) of methanol and chloroform (1/10), stirred at room temperature for one hour, collected by filtration, washed with two portions of chloroform, and then suspended in ethanol (50 mL). The suspension was stirred at room temperature for 3 hours and filtered, to obtain 4.70 g of the titled compound as a yellow crystalline product. The methanol-chloroform washings and the ethanol washings were combined and concentrated under reduced pressure to obtain 0.5 g of a yellow crystalline product. Thus obtained crystalline product was suspended in ethanol (50 mL). The suspension was heated under refluxing for several minutes, and then stirred at room temperature 3 hours. The precipitated crystalline product was collected by filtration and washed two portions of ethanol (1 mL), to obtain.0.43 g of the titled compound as a yellow crystalline product. Total amount: 5.13 g (yield 83%).

m.p.: 283-288° C. (decomp.)

$^1$H-NMR (DMSO-$d_6$), δ: 7.08 (1H, d, J=9 Hz), 7.3-7.5 (3H, m), 7.70 (1H, d, J=9 Hz), 8.25 (1H, dd, J=2 Hz, 9 Hz), 8.26 (1H, s), 8.66 (1H, d, J=2 Hz), 12.93 (1H, s).

IR (KBr) cm$^{-1}$: 3078, 1697, 1618, 1570, 1535, 1506, 1473, 1450, 1348, 1340, 1306, 1254, 1246, 1227, 1225, 1159, 758.

FAB-MS (m/e): 401 (M+1).

Example 19

2-[4-(2-Chlorophenoxy)-3-nitrophenyl]-4-hydroxythiazolo[5,4-d]pyrimidine potassium salt To a suspension of the above-mentioned 2-[4-(2-chlorophenoxy)-3-nitrophenyl]-4-hydroxythiazolo[5,4-d]pyrimidine (800 mg, 2.00 mol) in ethanol (32 mL) were added 0.5 mol/L potassium hydroxide/ethanol solution (6 mL) and ethanol (8 mL). The resulting mixture was stirred at room temperature for 22 hours. The precipitated crystalline product was collected by filtration, washed with ethanol (6 mL), and dried at room temperature under reduced pressure, to obtain 870 mg (yield 99%) of the titled compound as an orange crystalline product.

m.p.: 195-205° C. (decomp.)

$^1$H-NMR (DMSO-$d_6$, 400 MHz), δ: 7.07 (1H, d, J=9 Hz), 7.3-7.4 (2H, m), 7.4-7.5 (1H, m), 7.6-7.7 (1H, m), 7.96 (1H, s), 8.15 (1H, dd, J=2 Hz, 9 Hz), 8.55 (1H, d, J=2 Hz).

IR (KBr) cm$^{-1}$: 3629, 3388, 3213, 2347, 1618, 1578, 1537, 1508, 1473, 1338, 1265, 752.

FAB-MS (m/e): 439 (M+1).

Example 20

2-[4-(3-Fluorophenoxy)-3-nitrophenyl]-4-hydroxythiazolo[5,4-d]pyrimidine

To a solution of 3-fluorophenol (18 mg, 0.16 mmol) in DMSO (2 mL) was added 60% sodium hydride (13 mg, 0.33 mmol) under ice-cooling. The mixture was stirred at room temperature for 30 minutes. After addition of the aforementioned 2-(4-chloro-3-nitrophenyl)-4-hydroxy-thiazolo[5,4-d]pyrimidine (40 mg, 0.13 mmol), the mixture was stirred at room temperature for 46 hours. To the mixture was then added ice-water (5 mL) and 1M aqueous hydrochloric acid until the mixture reached pH 4.. The precipitated crystalline product was collected by filtration, washed successively with water (5 mL) and ether (5 mL), and dried at room temperature under reduced pressure. The crystalline product was purified by silica gel column chromatography (methanol/chloroform), to obtain 40.3 mg (yield 66%) of the titled compound as a pale yellow crystalline product.

$^1$H-NMR (DMSO-$d_6$, 400 MHz), δ: 7.05 (1H, dd, J=2 Hz, 8 Hz), 7.1-7.2 (2H, m), 7.35 (1H, d, J=9 Hz), 7.4-7.6 (1H, m), 8.27 (1H, s), 8.30 (1H, dd, J=2 Hz, 9 Hz), 8.66 (1H, d, J=2 Hz), 12.94 (1H, s).

FAB-MS (m/e): 385 (M+1).

Examlple 21

2-[4-(2-Fluorophenoxy)-3-nitrophenyl]-4-hydroxythiazolo[5,4-d]pyrimidine

In a nitrogen atmosphere, 2-fluorophenol (1.47 g, 16.0 mmol) was dissolved in DMSO (41 mL), and to the solution was added under ice-cooling 60% sodium hydride (1.33 g, 33.3 mmol). The resulting mixture was stirred at room temperature for 45 minutes. To the mixture was added under ice-cooling the aforementioned 2-(4-chloro-3-nitrophenyl)-4-hydroxythiazolo[5,4-d]pyrimidine (4.10 g, 13.3 mmol). The mixture was then stirred at room temperature for 40 hours. To the mixture were added ice-water (123 mL) and 1M aqueous hydrochloric acid until the mixture reached pH 3. The precipitated crystalline product was collected by filtration and washed with water (123 mL). Thus obtained crude crystalline product was dried under reduced pressure and purified by silica gel column chromatography (methanol/chloroform) and by repeated washing with a mixture of methanol and chloroform. The obtained crystalline product was dried at 40° C. under reduced pressure, to obtain 2.31 g (yield 59%) of the titled compound as a yellow crystalline product.

m.p.: 279-281° C. (decomp.)

$^1$H-NMR (DMSO-$d_6$, 400 MHz), δ: 7.19 (1H, d, J=9 Hz), 7.3-7.6 (4H, m), 8.25 (1H, s), 8.26 (1H, dd, J=2 Hz, 9 Hz), 8.65 (1H, d, J=2 Hz), 12.93 (1H, s).

IR (KBr) cm$^{-1}$: 3039, 2372, 2345, 1689, 1622, 1572, 1535, 1498, 1473, 1350, 1284, 1236, 1176, 1103, 1080, 1016, 970, 910, 845, 843, 781, 762, 708.

FAB-MS (m/e): 385 (M+1).

Example 22

2-[4-(2-Fluorophenoxy)-3-nitrophenyl]-4-hydroxythiazolo[5,4-d]pyrimidine potassium salt The above-mentioned 2-[4-(2-fluorophenoxy)-3-nitrophenyl]-4-hydroxythiazolo[5,4-d]pyrimidine (206 mg, 0.54 mmol) was suspended in ethanol (8 mL). After addition of 0.5 mol/L potassium hydroxide in ethanol (1.6 mL) and ethanol (2 mL), the suspension was stirred at room temperature for 17 hours. The precipitated crystalline product was collected by filtration, washed with ethanol (6 mL), and dried at room temperature under reduced pressure, to obtain 219 mg (yield 96w) of the titled compound as a yellow crystalline product.

m.p.: 175-185° C. (decomp.)

$^1$H-NMR (DMSO-$d_6$, 400 MHz), δ: 7.17 (1H, d, J=9 Hz), 7.3-7.4 (3H, m), 7.4-7.5 (1H, m), 7.95 (1H, s), 8.15 (1H, dd, J=2 Hz, 9 Hz), 8.53 (1H, d, J=2 Hz).

IR (KBr) cm$^{-1}$: 3629, 3107, 1620, 1574, 1539, 1498, 1481, 1346, 1342, 1282, 1242, 758.

FAB-MS (m/e): 423 (M+1).

Example 23

2-[4-(4-Chlorophenoxy)-3-cyanophenyl]-4-hydroxythiazolo[5,4-d]pyrimidine

In a nitrogen atmosphere, the aforementioned 2-(4-chloro-3-cyanophenyl)-4-hydroxythiazolo[5,4-d]pyrimidine (30 mg, 0.10 mmol) and 4-chlorophenol (20 mg, 0.16 mmol) were suspended in DMSO (5 mL). After addition of 60% sodium hydride (12 mg, 0.30 mmol) under ice-cooling, the suspension was stirred at room temperature for 48 hours. After further addition of 4-chlorophenol (15 mg, 0.12 mmol), DMSO (3 mL) and 60% sodium hydride (10 mg, 0.25 mmol) under ice-cooling, the suspension was stirred at room temperature for 18 hours. After further addition of 4-chlorophenol (15 mg, 0.12 mmol), DMSO (3 mL) and 60% sodium hydride (10 mg, 0.25 mmol) under ice-cooling, the suspension was stirred at room temperature for 18 hours. To the suspension were added ice-water (10 mL) and 1M aqueous hydrochloric acid, until the suspension reached pH 2. The precipitated crystalline product was collected by filtration and washed with water (5 mL×3). Thus obtained crude crystalline product was purified by silica gel column chromatography (methanol/chloroform), to 9 mg (yield 23%) of the titled compound as a white crystalline product.

$^1$H-NMR (CD$^3$OD/CDCl$_3$=1/10, 400 MHz), δ: 6.95 (1H, d, J=9 Hz), 7.1-7.2 (2H, m), 7.4-7.5 (2H, m), 8.05 (1H, s), 8.18 (1H, dd, J=2 Hz, 9 Hz), 8.38 (1H, d, J=2 Hz).

FAB-MS (m/e): 381 (M+1).

Example 24

2-[4-(4-Chlorophenoxy)-3-cyanophenyl]-4-hydroxythiazolo[5,4-d]pyrimidine potassium salt The above-mentioned 2-[4-(4-chlorophenoxy)-3-cyanophenyl]-4-hydroxythiazolo[5,4-d]pyrimidine (100 mg, 0.26 mmol) was suspended in ethanol (2 mL). After addition of 0.5 mol/L potassium hydroxide in ethanol (0.53 mL, 0.26 mmol), the suspension was stirred overnight at room temperature. The precipitated solid product was collected by filtration, washed with ethanol, and dried in air, to obtain 89 mg (yield 81%) of the titled compound as a yellow crystalline product.

m.p.: 245° C. (decomp.)

$^1$H-NMR (DMSO-d$_6$, 400 MHz), δ: 7.09 (1H, d, J=9 Hz), 7.30 (2H, d, J=9 Hz), 7.56 (2H, d, J=9 Hz), 8.07 (1H, s), 8.21 (1H, dd, J=2 Hz, 9Hz), 8.41 (1H, d, J=2 Hz).

IR (KBr) cm$^{-1}$: 2229, 1697, 1606, 1568, 1483, 1456, 1390, 1333, 1269, 1198, 1161, 1130, 1086, 1014, 982, 895, 849, 825, 802, 694, 590, 555, 515, 490.

FAB-MS (m/e): 419 (M+1).

Example 25

4-Hydroxy-2-[4-(4-methoxycarbonylphenoxy)-3-nitrophenyl]thiazolo[5,4-d]pyrimidine To a suspension of 60% sodium hydride (40 mg, 1.00 mmol) in DMSO (2 mL) was added methyl 4-hydroxybenzoate (122 mg, 0.80 mmol), and the mixture was stirred at room temperature for one hour. After addition of the aforementioned 2-(4-chloro-3-nitrophenyl)-4-hydroxythiazolo-[5,4-d]pyrimidine (62 mg, 0.20 mmol), the mixture was stirred at room temperature for 1.5 hours, and then at 50° C. for 42 hours. To the reaction mixture were added 2M hydrochloric acid (0.5 mL) and then water (1.5 mL) under water-cooling, and the mixture was stirred under water-cooling for one hour. The precipitated crystalline product was collected by filtration and washed successively with water and ether, to obtain 73 mg (yield 85%) of the titled compound as a pale brown crystalline product.

$^1$H-NMR (CDCl$_3$): δ: 3.93 (3H, s), 7.13 (2H, d, J=9 Hz), 7.18 (1H, d, J=9 Hz), 8.10 (1H, s), 8.11 (2H, d, J=9 Hz), 8.27 (1H, dd, J=2 Hz, 9 Hz), 8.67 (1H, d, J=2 Hz), 10.33 (1H, s)

IR (KBr) cm$^{-1}$: 3412, 2927, 1718, 1685, 1601, 1572, 1537, 1502, 1466, 1433, 1352, 1282, 1163, 1117, 766.

FAB-MS (m/e): 425 (M+1).

Example 26

2-[4-(4-Carboxyphenoxy)-3-nitrophenyl]-4-hydroxythiazolo[5,4-d]pyrimidine

The aforementioned 4-hydroxy-2-[4-(4-methoxycarbonylphenoxy)-3-nitrophenyl]thiazolo[5,4-d]pyrimidine (42 mg, 0.10 mmol) was suspended in methanol (4 mL). After addition of 1M aqueous sodium hydroxide (1 mL), the suspension was stirred at room temperature for 19 hours. Further, after addition of water (3 mL), the suspension was stirred at room temperature for 4-hours. The reaction mixture was washed with ethyl acetate, and 2M hydrochloric acid (1 mL) was added to the mixture. The precipitated crystalline product was collected by filtration, washed successively with water, ethanol, acetone, ethyl acetate, warm chloroform, and hexane, to obtain 20 mg (yield 48%) of the titled compound as a brown crystalline product.

$^1$H-NMR (DMSO-d$_6$), δ: 7.25 (2H, d, J=9 Hz), 7.44 (1H, J=9 Hz), 8.02 (2H, d, J=9 Hz), 8.27 (1H, s), 8.33 (1H, dd, J=2 Hz, 9 Hz), 8.69 (1H, d, J=2 Hz), 12.95 (1H, s).

FAB-MS (m/e): 411 (M+1).

Example 27

2-[4-(4-Carboxyphenoxy)-3-nitrophenyl]-4-hydroxythiazolo[5,4-d]pyrimidine dipotassium salt The above-mentioned 2-[4-(4-carboxyphenoxy)-3-nitrophenyl]-4-hydroxythiazolo[5,4-d]pyrimidine (300 mg, 0.73 mmol) was suspended in ethanol (10 mL). After addition of 0.5 mol/L potassium hydroxide/ethanol solution (3.0 mL) and ethanol (3 mL), the suspension was stirred at room temperature for one hour. The precipitated crystalline product was collected by filtration, washed with ethanol (10 mL), and dried at room temperature under reduced pressure, to obtain 345 mg (yield 97%) of the titled compound as an orange crystalline product.

m.p.: 270° C. (decomp.)

$^1$H-NMR (DMSO-d$_6$, 400 MHz), δ: 7.02 (2H, d, J=8 Hz), 7.17 (1H, d, J=9 Hz), 7.91 (2H, d, J=8 Hz), 7.96 (1H, s), 8.14 (1H, dd, J=1 Hz, 9 Hz), 8.51 (1H, d, J=1 Hz).

IR (KBr) cm$^{-1}$: 3381, 3278, 2345, 1614; 1564, 1537, 1481, 1392, 1350, 1279, 1227, 1192, 1161.

FAB-MS (m/e): 487 (M+1).

Example 28

2-[3-Nitro-4-(4-phenoxyphenoxy)phenyl]-4-hydroxythiazolo[5,4-d]pyrimidine

In a nitrogen atmosphere, 4-phenoxyphenol (32 mg, 0.17 mmol) was dissolved in DMSO (3 mL), and after addition of 60% sodium hydride (13 mg, 0.33 mmol) under ice-cooling, the resulting solution was stirred at room temperature for 30 minutes. Then, after addition of 2-(4-chloro-3-nitrophenyl)-4-hydroxythizolo[5,4-d]pyrimidine (40 mg, 0.13 mmol), the solution was stirred at room 35 temperature for 18 hours. To the solution were added ice-water (10 mL) and 1M aqueous hydrochloric acid until the solution reached pH 3. The precipitated crystalline product was collected by filtration, and washed with water (5 mL×5) and ether (5 mL×5). Thus obtained crude crystalline product was purified by silica gel column chromatography (methanol/chloroform), to obtain 35 mg (yield 59%) of the titled compound as a yellow crystalline product.

¹H-NMR (DMSO-d$_6$, 400 MHz), δ: 7.0-7.3 (8H, m), 7.4-7.5 (2H, m), 8.25 (1H, s), 8.26 (1H, dd, J=2 Hz, 9 Hz), 8.62 (1H, d, J=2 Hz), 12.92 (1H, s).
IR (KBr) cm$^{-1}$: 3423, 3064, 2927, 2372, 1686, 1618, 1572, 1535, 1487, 1483, 1466, 1350, 1267, 1236, 1186, 1084, 860, 692.
FAB-MS (m/e): 459 (M+1).

Example 29

2-(3-Nitro-4-phenylaminophenyl)-4-hydroxy-thiazolo[5,4-d]pyrimidine

Aniline (0.5 mL, 5.5 mmol), 2-(4-chloro-3-nitro-phenyl)-4-hydroxythiazolo[5,4-d]pyrimidine (31 mg, 0.10 mmol), potassium carbonate (28 mg, 0.20 mmol), and copper oxide (1 mg) were heated under refluxing for 2 hours. The mixture was cooled to room temperature. Subsequently, to the mixture were added ice-water (10 mL) and 1M aqueous hydrochloric acid until the mixture reached pH 3. The precipitated crystalline product was collected by filtration, washed with water (3 mL×5) and ether (3 mL×2), and dried at 50° C. under reduced pressure, to obtain 33 mg (yield 89%) of the titled compound as a brown crystalline product.
¹H-NMR (DMSO-d$_6$, 400 MHz), δ: 7.26 (1H, d, J=9 Hz), 7.3-7.5 (5H, m), 8.06 (1H, dd, J=2 Hz, 9Hz), 8.21 (1H, d, J=4 Hz), 8.68 (1H, d, J=2 Hz), 9.77 (1H, s), 12.85 (1H, s).
IR (KBr) cm$^{-1}$: 3408, 3064, 2372, 1686, 1624, 1595, 1568, 1533, 1497, 1475, 1352, 1263, 1215, 1153, 1072,. 972, 760, 694.
FAB-MS (m/e): 366 (M+1).

Example 30

4-Hydroxy-2-[4-(4-isopropylphenoxy)-3-nitro-phenyl]thiazolo[5,4-d]pyrimidine

To a suspension of 60% sodium hydride (10 mg, 0.25 mmol) in DMSO (2 mL) was added 4-isopropylphenol (21 mg, 0.15 mmol). The suspension was stirred at room temperature for one hour. Then, after addition of the aforementioned 2-(4-chloro-3-nitrophenyl)-4-hydroxythiazolo[5,4-d]pyrimidine (31 mg, 0.1 mmol), the suspension was stirred at room temperature for 21 hours. After addition of 1M hydrochloric acid (0.5 mL) and water (1.5 mL) under water-cooling, the reaction mixture was stirred for 30 minutes. The precipitated crystalline product was collected by filtration, and washed successively with water, ether and hexane, to obtain 32 mg (yield 78%) of the titled compound as a yellow crystalline product.
¹H-NMR (DMSO-d$_6$), δ: 1.23 (6H, d, J=7 Hz), 2.9-3.0 (1H, m), 7.14 (2H, d, J=9 Hz), 7.19 (1H, d, J=9 Hz), 7.36 (2H, d, J=9 Hz), 8.25 (1H, dd, J=2 Hz, 9 Hz), 8.26 (1H, s), 8.62 (1H, d, J=2 Hz), 12.92 (1H, s).
IR (KBr) cm$^{-1}$: 2958, 1697, 1618, 1599, 1568, 1537, 1504, 1454, 1352, 1302, 1267, 1248, 1225, 1200, 1167, 1165, 850.
FAB-MS (m/e): 409 (M+1).

Example 31

4-Hydroxy-2-[3-nitro-4-(4-phenylphenoxy)-phenyl]thiazolo[5,4-d]pyrimidine

To a suspension of 60% sodium hydride (10 mg, 0.25 mmol) in DMSO (2 mL) was added 4-phenylphenol (26 mg, 0.15 mmol). The suspension was then stirred at room temperature for 2 hours. After addition of the aforementioned 2-(4-chloro-3-nitrophenyl)-4-hydroxythiazolo[5,4-d]pyrimidine (31 mg, 0.1 mmol), the suspension was stirred at room temperature for 40 hours. Then, after addition of 1M hydrochloric acid (0.5 mL) and water (1.5 mL) under water-cooling, the reaction mixture was stirred for 30 minutes. The precipitated crystalline product was collected by filtration and washed successively with water, ether and hexane, to obtain 34 mg (yield 77%) of the titled compound as a yellow crystalline product.
¹H-NMR (DMSO-d$_6$), δ: 7.3-7.5 (6H, m), 7.69 (2H, d, J=8 Hz), 7.78 (2H, d, J=8 Hz), 8.26 (1H, s), 8.29 (1H, dd, J=2 Hz, 9 Hz), 8.66 (1H, d, J=2 Hz), 12.93 (1H, s).
IR (KBr) cm$^{-1}$: 3059, 1676, 1672, 1618, 1600, 1571, 1535, 1514, 1485, 1466, 1350, 1250, 1167, 766.
FAB-MS (m/e): 443 (M+1).

Example 32

4-Hydroxy-2-[3-nitro-4-(3-pyridyloxy)-phenyl]thiazolo[5,4-d]pyrimidine

To a suspension of 60% sodium hydride (26 mg, 0.65 mmol) in DMSO (1 mL) was added 3-hydroxypyridine (62 mg, 0.65 mmol). The suspension was then stirred at room temperature for one hour. After addition of the aforementioned 2-(4-chloro-3-nitrophenyl)-4-hydroxythiazolo-[5,4-d]pyrimidine (100 mg, 0.32 mmol), the suspension was stirred at room temperature for 91.5 hours. To the reaction mixture were added successively ice-water (0.1 mL) and 1 mol/L hydrochloric acid, until the mixture reached pH 7. The precipitated crystalline product was collected by filtration and washed with water (3 mL). Thus obtained crude crystalline product was purified by silica gel column chromatography (methanol/chloroform), to obtain 100 mg (yield 85%) of the titled compound as a yellow crystalline product.
m.p.: 276-280° C. (decomp.)
¹H-NMR (DMSO-d$_6$, 400 MHz), δ: 7.34 (1H, d, J=9 Hz), 7.53 (1H, dd, J=5 Hz, 8 Hz), 7.6-7.7 (1H, m), 8.26 (1H, s), 8.29 (1H, dd, J=2 Hz, 9 Hz), 8.5-8.6 (1H, m), 8.55 (1H, d, J=3 Hz), 8.67 (1H, d, J=2 Hz).
IR (KBr) cm$^{-1}$: 3055, 2648, 1701, 1699, 1616, 1572, 1570, 1537, 1466, 1427, 1350, 1269, 1219, 1217, 1215, 1140.
FAB-MS (m/e): 368 (M+1).

Example 33

4-Hydroxy-2-[3-nitro-4-(3-pyridyloxy)-phenyl]thiazolo[5,4-d]pyrimidine potassium salt To a suspension of the above-mentioned 4-hydroxy-2-[3-nitro-4-(3-pyridyloxy)phenyl]thiazolo[5,4-d]pyrimidine (50 mg, 0.14 mol) in ethanol (2 mL) was added 0.5 mol/L potassium hydroxide in ethanol (0.34 mL). The suspension was stirred at room temperature for 4 hours. The precipitated crystalline product was collected by filtration, washed with ethanol (0.5 mL×2), dried at room temperature under reduced pressure, to obtain 50.5 mg (yield 89%) of the titled compound as a pale yellow crystalline product.
m.p.: 236-240° C. (decomp.)
¹H-NMR (DMSO-d$_6$, 400 MHz): 7.32 (1H, d, J=9 Hz), 7.50 (1H, dd, J=5 Hz, 8 Hz), 7.6-7.7 (1H, m), 7.95 (1H, s), 8.18 (1H, dd, J=2 Hz, 9 Hz), 8.48 (1H, dd, J=1 Hz, 5 Hz), 8.53 (1H, d, J=3 Hz), 8.56 (1H, d, J=2 Hz).
IR (KBr) cm$^{-1}$: 3358, 3064, 1618, 1574, 1539, 1477, 1425, 1344, 1302, 1296, 1269, 1207.
FAB-MS (m/e): 406 (M+1).

Reference Example 12

4-Methoxymethoxyphenol

A mixture of 60% sodium hydride (1.80 g, 45.0 mmol) and dry THF (20 mL) was cooled to −20° C. After addition of a solution of hydroquinone (2.00 g, 18.2 mmol) in THF (30 mL), the mixture was stirred at room temperature for one hour and then cooled again to −20° C. After dropwise addition of chloromethyl methyl ether (1.3 mL, 18.0 mmol), the cooled mixture was slowly warmed to 10° C., stirred at room temperature for one hour, and poured onto ice pieces (500 g). To the resulting mixture was added 3 mol/L aqueous hydrochloric acid until the mixture reached pH 4-5. Subsequently, the mixture was subjected to extraction with dichloromethane (100 mL×2). The extract was washed with water (100 mL×2) and saturated aqueous sodium chloride (100 mL), dried over anhydrous sodium sulfate, and placed under reduced pressure to distill the solvent off. The residue was purified by silica gel column chromatography (ethyl acetate/hexane), to obtain 581 mg (yield 21%) of the titled compound as pale yellow oil.

$^1$H-NMR (CDCl$_3$, 400 MHz), δ: 3.47 (3H, s), 5.09 (2H, s), 6.7-6.8 (2H, m), 6.9-7.0 (2H, m).

Example 34

4-Hydroxy-2-[4-(4-methoxymethoxyphenoxy)-3-nitrophenyl]thiazolo[5,4-d]pyrimidine To a suspension of 60% sodium hydride (26 mg, 0.65 mmol) in DMSO (1 mL) was added the above-mentioned 4-methoxymethoxyphenol (100 mg, 0.65 mmol). The suspension was stirred at room temperature for 30 minutes. After addition of the aforementioned 2-(4-chloro-3-nitro-phenyl)-4-hydroxythiazolo[5,4-d]pyrimidine (100 mg, 0.32 mmol), the suspension was stirred at room temperature for 72.5 hours. To the reaction mixture were added ice-water (1 mL) and 1 mol/L hydrochloric acid, until the mixture reached pH 7. The precipitated crystalline product was collected by filtration and washed with water (3 mL). Thus obtained crude crystalline product was purified by silica gel column chromatography (methanol/chloroform), to obtain 126 mg (yield 92%) of the titled compound as a yellow crystalline product.

m.p.: 235-236° C.

$^1$H-NMR (DMSO-d$_6$, 400 MHz), δ: 3.41 (3H, s), 5.21 (2H, s), 7.1-7.3 (5H, m), 8.2-8.3 (2H, m), 8.61 (1H, d, J=1 Hz), 12.91 (1H, s).

Example 35

4-Hydroxy-2-[4-(4-hydroxyphenoxy)-3-nitro-phenyl]thiazolo[5,4-d]pyrimidine

A suspension of the above-mentioned 4-hydroxy-2-[4-(4-methoxymethoxyphenoxy)-3-nitrophenyl]thiazolo[5,4-d]pyrimidine (75 mg, 0.18 mmol) in THF (18 mL) were added a solution (0.6 mL, 2.40 mmol) of 4 mol/L hydrochloric acid in dioxane and water (five drops). The suspension was stirred at room temperature for 41 hours, at 50° C. for 2 hours, heated under refluxing for one hour, and then placed under reduced pressure to distill the solvent off. To the residue was added ethanol (1.5 mL). The precipitated crystalline product was collected by filtration, washed with ethanol (0.5 mL) and hexane (2 mL), and dried at 50° C. for one hour under reduced pressure, to obtain 67 mg (yield 97%) of the titled compound as a yellow crystalline product.

m.p.: >300° C. (decomp.)

$^1$H-NMR (DMSO-d$_6$, 400 MHz), δ: 6.8-6.9 (2H, m), 7.0-7.1 (3H, m), 8.21 (1H, dd, J=2 Hz, 9 Hz), 8.25 (1H, s), 8.59 (1H, d, J=2 Hz), 9.59 (1H, s), 12.91 (1H, s).

IR (KBr) cm$^{-1}$: 3207, 2893, 1682, 1622, 1570, 1537, 1508, 1468, 1443, 1344, 1306, 1252, 1228, 1194, 1101, 1018, 831.

FAB-MS (m/e): 383 (M+1).

Example 3

2-[3-Cyano-4-(4-fluorophenoxy)phenyl]-4-hydroxythiazolo[5,4-d]pyrimidine

To a suspension of 60% sodium hydride (122 mg, 3.05 mmol) in DMSO (4 mL) was added 4-fluorophenol (342 mg, 3.05 mmol), and the suspension was stirred at room temperature for one hour. After addition of the aforementioned 2-(4-chloro-3-cyanophenyl)-4-hydroxythiazolo[5,4-d]pyrimidine (400 mg, 1.39 mmol), the suspension was stirred at room temperature for 46 hours and then at 60° C. for 9 hours. To the suspension was added under ice-cooling 1 mol/L hydrochloric acid until the suspension reached pH 3. The precipitated crystalline product was collected by filtration, washed successively with water (10 mL×3), ethanol (5 mL) and ether (6 mL×2), and dried at 50° C. under reduced pressure for one hour, to obtain 466 mg (yield 92%) of the titled compound as a brownish white crystalline product.

m.p.: >290° C. (decomp.)

$^1$H-NMR (DMSO-d$_6$, 400 MHz), δ: 7.03 (1H, d, J=9 Hz), 7.3-7.4 (4H, m), 8.2-8.3 (2H, m), 8.50 (1H, d, J=2 Hz), 12.91 (1H, s).

IR (KBr) cm$^{-1}$: 2235, 1678, 1608, 1577, 1498, 1477, 1369, 1354, 1263, 1221, 1186, 1111, 1103, 1016, 972, 906, 854, 841, 839, 796, 794, 764, 710, 677, 648, 611, 565, 507.

Example 37

2-[3-Cyano-4-(4-fluorophenoxy)phenyl]-4-hydroxythiazolo[5,4-d]pyrimidine potassium salt To a suspension of the above-mentioned 2-[3-cyano-4-(4-fluorophenoxy)phenyl]-4-hydroxythiazolo[5,4-d]pyrimidine (466 mg, 1.28 mmol) in ethanol (14 mL) was added a solution (2.8 mL) of 0.5 mol/L potassium hydroxide in ethanol, and the suspension was stirred at room temperature for one hour. The precipitated crystalline product was collected by filtration, washed with ethanol (6 mL) and dried at room temperature under reduced pressure, to obtain 411 mg (yield 80%) of the titled compound as a pale yellow crystalline product.

m.p.: 257-262° C. (decomp.)

$^1$H-NMR (DMSO-d$_6$, 400 MHz), δ: 7.01 (1H, d, J=9 Hz), 7.3-7.4 (4H, m), 7.93 (1H, s), 8.16 (1H, dd, J=2 Hz, 9 Hz), 8.33 (1H, d, J=2 Hz).

IR (KBr) cm$^{-1}$: 2227, 1641, 1566, 1481, 1390, 1331, 1292, 1275, 1227, 1188, 1138, 1107, 1026, 831, 829.

FAB-MS (m/e): 403 (M+1).

Reference Example 13

4-(4-Fluorophenoxy)-3-nitrobenzoic acid anhydride

A solution comprising 4-(4-fluorophenoxy)-3-nitro-benzoic acid (8.0 g, 28.9 mmol), thionyl chloride (10.3 g, 86.6 mmol), DMF (two drops), and dichloromethane (80 mL) was heated under refluxing for 3 hours. Subsequently, the solution was placed under reduced pressure to distill the solvent off, and after addition of benzene and toluene, concentrated to dryness. To the reside were added dichloromethane (50 mL) and 4-(4-fluorophenoxy)-3-nitrobenzoic acid (8.0 g, 28.9 mmol). To the resulting mixture were dropwise added a solution of triethylamine (5.84 g, 57.7 mmol) in dichloromethane (30 mL) under ice-cooling and stirring, and the mixture was stirred over-night at room temperature. Subsequently, the mixture was placed under reduced pressure to distill the solvent off. To the reside was added water. The precipitated solid product was collected by filtration and dried under reduced pressure, to obtain 12.6 g (yield 81%) of the titled compound as a yellow crystalline product.

Thus obtained product was per se subjected to the following. reaction.

Example 38

2-[4-(4-Fluorophenoxy)-3-nitrophenyl]-4-hydroxyoxazolo[5,4-d]pyrimidine

A mixture of 5-amino-4,6-dihydroxypyrimidine hydrochloride (500 mg, 3.06 mmol) and the above-mentioned 4-(4-fluorophenoxy)-3-nitrobenzoic acid anhydride (8.2 g, 15.3 mmol) was heated in an oil bath (heated to 155° C.) for 1.5 hours in a nitrogen stream. After addition of chloroform, the reaction mixture was stirred overnight at room temperature. Subsequently, the insolubles were filtered off, and the filtrate was placed under reduced pressure to distill the solvent off. This procedure was repeated twice. The obtained crude product was subjected to silica gel column chromatography and eluted with chloroform/methanol (100/1), to collect a portion of the titled compound. The collected portion was concentrated and washed with diethyl ether, to obtain 420 mg (yield 82%) of the titled compound as a white crystalline product.

$^1$H-NMR (DMSO-$d_6$, 400 MHz), δ: 7.18 (1H, d, J=9 Hz), 7.3-7.4 (4H, m), 8.30 (1H, s), 8.31 (1H, dd, J=2 Hz, 9 Hz), 8.66 (1H, d, J=2 Hz), 13.04 (1H, s).

Example 39

2-[4-(4-Fluorophenoxy)-3-nitrophenyl]-4-hydroxyoxazolo[5,4-d]pyrimidine potassium salt To a suspension of the above-mentioned 2-[4-(4-fluorophenoxy)-3-nitrophenyl]-4-hydroxyoxazolo[5,4-d]-pyrimidine (400 mg, 1.09 mmol) in ethanol (8 mL) was added a solution (2.17 mL, 1.09 mmol) of 0.5 mol/L potassium hydroxide in ethanol, and the suspension was stirred at room temperature for 3 hours. The precipitated solid product was collected by filtration, washed with ethanol, and dried overnight at 40° C. under reduced pressure, to obtain 420 mg (yield 95%) of the titled compound as a yellow crystalline product.

m.p.: >260° C. (decomp.)

$^1$H-NMR (DMSO-$d_6$, 400 MHz), δ: 7.17 (1H, d, J=9 Hz), 7.2-7.4 (4H, m), 7.88 (1H, s), 8.22 (1H, dd, J=2 Hz, 9 Hz), 8.56 (1H, d, J=2 Hz).

IR (KBr) cm$^{-1}$: 1625, 1506, 1533, 1349, 1275, 1228, 1188, 1161, 1014, 908, 848, 817, 815, 782, 727.

Example 40

2-[3-Cyano-4-(4-fluorophenoxy)phenyl]-4-methoxythiazolo[5,4-d]pyrimidine

To a suspension of 55% sodium hydride (64 mg, 1.47 mmol) in DMSO (2 mL) was added 4-fluorophenol (163 mg, 1.45 mmol), and the suspension was stirred at room temperature for one hour. After addition of the aforementioned 2-(4-chloro-3-cyanophenyl)-4-methoxythiazolo[5,4-d]pyrimidine (400 mg, 1.32 mmol) and DMSO (2 mL), the suspension was stirred at room temperature for 6.5 hours and then at 50° C. for 16 hours. To the suspension was added water (40 mL) under ice-cooling. The precipitated crystalline product was collected by filtration and washed with water (10 mL). The obtained crude crystalline product was purified by silica-gel column chromatography (ethyl acetate/hexane). Thus purified crystalline product was washed with a mixture of ethyl acetate and hexane and hexane, and dried at room temperature in air, to obtain 450 mg (yield 90%) of the titled compound as a brownish white crystalline product.

m.p.: 205.6-206.6° C.

$^1$H-NMR (DMSO-$d_6$, 400 MHz), δ: 4.27 (3H, s), 6.89 (1H, d, J=9 Hz), 7.1-7.2 (4H, m), 8.15 (1H, dd, J=2 Hz, 8 Hz), 8.44 (1H, d, J=2 Hz), 8.83 (1H, s).

IR (KBr) cm$^{-1}$: 2239, 1612, 1608, 1568, 1529, 1500, 1475, 1414, 1396, 1534, 1323, 1263, 1190, 1163, 1111, 1109, 1043.

FAB-MS (m/e): 379 (M+1).

Example 41

2-[3-Cyano-4-(4-fluorophenylthio)phenyl]-4-methoxythiazolo[5,4-d]pyrimidine

The aforementioned 2-(4-chloro-3-cyanophenyl)-4-hydroxythiazolo[5,4-d]pyrimidine (200 mg, 0.66 mmol), potassium carbonate (110 mg, 0.80 mmol), 4-fluorothiophenol (0.084 mL, 0.78 mmol), and ethanol (4 mL) were mixed and heated under refluxing for 6 hours in a nitrogen atmosphere. The mixture was then placed under reduced pressure to distill the solvent off. To the residue was added water (10 mL). The precipitated crystalline product was collected by filtration and purified by silica gel column chromatography (ethyl acetate/hexane, methanol/chloroform). Thus treated crystalline product was washed with a mixture of ethyl acetate and hexane and then hexane, and dried in air, to obtain 209 mg (yield 80%) of the titled compound as a pale yellow crystalline product.

m.p. 215° C.

$^1$H-NMR (CDCl$_3$, 400 MHz): 4.28 (3H, s), 7.01 (1H, d, J=9 Hz), 7.1-7.3 (2H, m), 7.5-7.7 (2H, m), 8.01 (1H, dd, J=2 Hz, 8 Hz), 8.40 (1H, d, J=2 Hz), 8.82 (1H, s).

Example 42

2-[3-Cyano-4-(4-fluorophenylthio)phenyl]-4-hydroxythiazolo[5,4-d]pyrimidine

In a suspension of the above-mentioned 2-[3-cyano-4-(4-fluorophenylthio)phenyl]-4-methoxythiazolo[5,4-d]-pyrimidine (200 g, 0.51 mmol) in dichloromethane (8 mL) was dropwise added boron tribromide (0.15 mL, 1.59 mmol). The suspension was then stirred at 40° C. for 4 hours, and to the suspension was added ice-water (8.5 mL). The precipitated crystalline product was collected by filtration, washed successively with dichloromethane (4 mL) and water (20 mL), and dried at room temperature under reduced pressure, to obtain 155 mg (yield 80w) of the titled compound as a pale yellow crystalline product.

m.p.: 326-331° C.

$^1$H-NMR (DMSO-$d_6$, 4, 400 MHz), δ: 7.16 (1H, d, J=8 Hz), 7.3-7.5 (2H, m), 7.6-7.8 (2H, m), 8.18 (1H, dd, J=2 Hz, 8 Hz), 8.25 (1H, d, J=3 Hz), 8.46 (1H, d, J=2 Hz), 12.92 (1H, s).

Example 43

2-[3-Cyano-4-(4-fluorophenylthio)phenyl]-4-hydroxythiazolo[5,4-d]pyrimidine potassium salt To a suspension of the above-mentioned 2-[3-cyano-4-(4-fluorophenylthio)phenyl]-4-hydroxythiazolo[5,4-d]-pyrimidine (120 mg, 0.32 mmol) in ethanol (6 mL) was added a solution (0.7 mL) of 0.5 mol/L potassium hydroxide in ethanol, and the suspension was stirred at room temperature for 22 hours. The precipitated crystalline product was collected by filtration, washed with ethanol (5 mL), and dried at room temperature under reduced pressure, to obtain 127 mg (yield 89%) of the titled compound as a pale yellow crystalline product.

m.p.: 293-298° C. (decomp.)
1H-NMR (DMSO-$d_6$, 400 MHz), δ: 7.21 (1H, d, J=9 Hz), 7.3-7.4 (2H, m), 7.6-7.7 (2H, m), 7.94 (1H, s), 8.09 (1H, dd, J=2 Hz, 9 Hz), 8.31 (1H, d, J=2 Hz).
IR (KBr) $cm^{-1}$: 3396, 3047, 2227, 1919, 1653, 1591, 1567, 1491, 1470, 1398, 1329, 1298, 1225, 1157, 1065, 984, 827.
FAB-MS (m/e): 419 (M+1).

Example 44

2-[3-Cyano-4-(2-fluorophenoxy)phenyl]-4-methoxythiazolo[5,4-d]pyrimidine

To a suspension of 55% sodium hydride (24 mg, 0.55 mmol) in DMSO (0.7 mL) was added 2-fluorophenol (62 mg, 0.55 mmol), and the suspension was stirred at room temperature for 30 minutes. After addition of the aforementioned 2-(4-chloro-3-cyanophenyl)-4-methoxythiazolo[5,4-d]pyrimidine (150 mg, 0.50 mmol) and DMSO (0.7 mL), the suspension was stirred at 50° C. for 15 hours. To the suspension were added 2-fluorophenol (31 mg, 0.27 mmol), 55% sodium hydride (12 mg, 0.27 mmol) and DMSO (0.4 mL), and the suspension was then stirred at 50° C. for 8 hours. To the suspension was further added water (9 mL) under ice-cooling. The precipitated crystalline product was collected by filtration, washed with water (4 mL), and purified by silica gel column chromatography (ethyl acetate/hexane), to obtain 174 mg (yield 84%) of the titled compound as a white crystalline product.

m.p.: 250.4-253.4° C.
$^1$H-NMR (CDCl$_3$, 400 MHz), δ: 4.27 (3H, s), 6.85 (1H, dd, J=1 Hz, 9 Hz), 7.2-7.4 (4H, m), 8.15 (1H, dd, J=2 Hz, 9 Hz), 8.45 (1H, d, J=2 Hz), 8.69 (1H, s).

Example 45

2-[3-Cyano-4-(2-fluorophenoxy)phenyl]-4-hydroxythiazolo[5,4-d]pyrimidine

To a suspension of the above-mentioned 2-[3-cyano-4-(2-fluorophenoxy)phenyl]-4-methoxythiazolo[5,4-d]pyrimidine (160 g, 0.42 mmol) in dichloromethane (6.4 mL) was dropwise added boron tribromide (0.12 mL, 1.27 mmol), and the suspension was stirred at 40° C. for 18 hours. After addition of ethyl acetate (0.2 mL), the suspension was stirred at the same temperature for 8 hours. Then, after addition of ice-water (2 mL), the suspension was placed under reduced pressure to distill the solvent off. To the reside was added water (20 mL), and the aqueous mixture was stirred at room temperature for one hour. The precipitated crystalline product was collected by filtration, washed with water (10 mL), and dried at room temperature under reduced pressure. The obtained crystalline product was suspended in ethanol (15 mL), stirred at room temperature for one hour, and collected by filtration. The collected cryralline product was washed with ethanol (5 mL) and dried at room temperature under reduced pressure, to obtain 128 mg (yield 80w) of the titled compound as a brownish white crystalline product.

m.p.: 288-293° C.
$^1$H-NMR (DMSO-$d_6$, 400 MHz), δ: 7.04 (1H, d, J=9 Hz), 7.3-7.6 (4H, m), 8.25 (1H, d, J=4 Hz), 8.28 (1H, dd, J=2 Hz, 9 Hz), 8.53 (1H, d, J=2 Hz), 12.91 (1H, s).

Example 46

2-[3-Cyano-4-(2-fluorophenoxy)phenyl]-4-hydroxythiazolo[5,4-d]pyrimidine potassium salt In a suspension of the above-mentioned 2-[3-cyano-4-(2-fluorophenoxy)phenyl]-4-hydroxythiazolo[5,4-d]pyrimidine (127 mg, 0.33 mmol) in ethanol (3.5 mL) was added a solution (0.73 mL) of 0.5 mol/L potassium hydroxide in ethanol, and the suspension was stirred at room temperature for 4 hours. The precipitated crystalline product was collected by filtration, washed with ethanol (2 mL), and dried at room temperature under reduced pressure, to obtain 117 mg (yield 88%) of the titled compound as a white crystalline product.

m.p.: 235-240° C. (decomp.)
$^1$H-NMR (DMSO-$d_6$, 400 MHz), δ: 7.00 (1H, d, J=9 Hz), 7.3-7.6 (4H, m), 7.94 .(1H, s), 8.17 (1H, dd, J=2 Hz, 9 Hz), 8.35 (1H, d, J=2 Hz).
IR (KBr) $cm^{-1}$: 3115, 2233, 1570, 1500, 1483, 1458, 1412, 1329, 1279, 1248, 1186, 1124, 1105, 1028, 987.
FAB-MS (m/e): 403 (M+1).

Example 47

2-(3-Cyano-4-phenoxyphenyl)-4-methoxy-thiazolo[5,4-d]pyrimidine

To a solution of phenol (93 mg, 0.99 mmol) in dry DMSO (20 mL) was added 600 sodium hydride (40 mg, 0.99 mmol), and the solution was stirred at 50° C. for 20 minutes. To the solution was added a solution of the aforementioned 2-[4-chloro-3-cyanophenyl]thiazolo[5,4-d]pyrimidine (150 mg, 0.50 mmol) in dry DMSO (4 mL). The resulting mixture was stirred at room temperature for 3 hours and further at 50° C. for 3 hours. To the reaction mixture was added water. Thus precipitated solid product was collected by filtration, washed with water, and dried in air, to obtain 152 mg (yield 85%) of the titled compound as a white crystalline product.

$^1$H-NMR (DMSO-$d_6$, 400 MHz), δ: 4.15 (3H, s), 7.04 (1H, d, J=9 Hz), 7.3-7.6 (5H, m), 8.35 (1H, dd, J=2 Hz, 9 Hz), 8.60 (1H,d, J=2 Hz), 8.76 (1H, s).

Example 48

2-(3-Cyano-4-phenoxyphenyl)-4-hydroxy-thiazolo[5,4-d]pyrimidine

To a suspension of the above-mentioned 2-(3-cyano-4-phenoxyphenyl)-4-methoxythiazolo[5,4-d]pyrimidine (150 mg, 0.42 mmol) in dry dichloromethane (10 mL) was added boron tribromide (313 mg, 1.25 mmol), and the suspension was stirred at room temperature for 66 hours. After addition of ethyl acetate (3 mL), the suspension was further stirred at 50° C. for 3 hours. To the reaction mixture was added ice-water. Thus precipitated solid product was collected by filtration, washed with water and ethyl acetate, and dried in air, to obtain 87 mg (yield 61%) of the titled compound as a white crystalline product.

$^1$H-NMR (DMSO-$d_6$, 400 MHz), δ: 7.03 (1H, d, J=9 Hz), 7.2-7.6 (5H, m), 8.2-8.3 (1H, m), 8.27 (1H, dd, J=2 Hz, 9 Hz), 8.50 (1H, d, J=2 Hz), 12.90 (1H, s).

Example 49

2-(3-Cyano-4-phenoxyphenyl)-4-hydroxy-thiazolo[5,4-d]pyrimidine potassium salt To a suspension of the above-mentioned 2-(3-cyano-4-phenoxyphenyl)-4-hydroxythiazolo[5,4-d]pyrimidine (85 mg, 0.25 mmol) in ethanol (2 mL) was added a solution (0.49 mL, 0.25 mmol) of 0.5 mol/L potassium hydroxide in ethanol, and the suspension was stirred overnight at room temperature. The precipitated solid product was collected by filtration, washed with ethanol, and dried in air, to obtain 72 mg (yield 77%) of the titled compound as a yellow crystalline product.

m.p.: >260° C. (decomp.)

$^1$H-NMR (DMSO-$d_6$, 400 MHz) δ: 7.02 (1H, d, J=9 Hz), 7.2-7.6 (5H, m), 8.01 (1H, s), 8.18 (1H, dd, J=2 Hz, 9 Hz), 8.37 (1H, d, J=2 Hz).

IR (KBr) cm$^{-1}$: 2231, 1668, 1560, 1481, 1392, 1331, 1263, 1192, 1163, 1113, 1072, 1020, 984, 895, 858, 804, 787, 690.

FAB-MS (m/e): 385 (M+1).

Example 50

Pharmacological Experiment 1 (In Vitro Measuring Method)

(Measuring Procedure)

1. Preparation of Test Sample

The test compound was dissolved in dimethylsulfoxide and diluted with 50 mM phosphate buffer (pH 7.5), to give a solution of a predetermined concentration.

2. Measurement

125 μL of each of the solutions of the test compound having different concentrations was added to 1 mL of a solution of Xanthine (SIGMA, 250 μM) in the 50 mM phosphor buffer (pH 7.5). The mixture was then pre-incubated at 30° C. for 5 min. Subsequently, to the pre-incubated mixture was added 125 μL of Cow milk Xanthine Oxidase (Roche) diluted with the 50 mM phosphate buffer (pH 7.5) to 70 mU/mL, and the mixture was subjected to reaction at 30° C. for 10 minutes. Then, 1N hydrochloric acid, (200 μL) was added to the reaction mixture to terminate the reaction. Subsequently, absorbance at OD 290 nm was measured by means of a spectrophotometer (Shimadzu UV-160A)., to obtain a inhibition ratio. The measured inhibition ration was used to obtain IC$_{50}$.

The inhibition ratio was calculated according to the following formula:

Inhibition ratio (%)=[1−(B−C)/(A−C)]×100

A: absorbance of control

B: absorbance measured on a sample containing test compound

C: absorbance of blank (Test Results)

The test results are set forth in Tables 11 and 12.

As is apparent from Tables 11 and 12, the compounds of the present invention show an excellent xanthine oxidase inhibiting action in in vitro pharmaccological test.

Example 51

Pharmacological Experiment 2 (In Vivo Test)

(Test Method)

The test compound suspended in 1% methylcellulose solution in an amount of 0.3 mg/kg or 3 mg/kg was administered to unfasted ICR mouse (7 W) by forced single oral administration. The blood was collected from main artery from the mouse under etherization after one hour from the administration. The plasma was separated from the collected blood in the conventional manner. The plasma was then subjected to measurement of uric acid value by the enzyme method by means of an automatic analytical apparatus (7060E), to obtain an in-plasma uric acid value-inhibition ratio in the test sample-administered group as compared with a ratio obtained in the normal group.

Based on the obtained in-plasma uric acid inhibition ratio, activity values (%) relative to activity values obtained in the simultaneously conducted tests using TMX-67 (0.3 mg/kg) or allopurinol (3 mg/kg).

(Test Results)

The test results are set forth in Tables 11 and 12.

As is apparent from Tables 11 and 12, the compounds of the present invention show an excellent xanthine oxidase inhibiting action in in vivo pharmaccological test.

TABLE 11

| Test compound (Example No.) | In Vitro IC$_{50}$ (nM) | In Vivo (%) allopurinol (3 mg/kg) | In Vivo (%) TMX-67 (0.3 mg/kg) |
|---|---|---|---|
| Example 2 | 13.8 | 90 | 27 |
| 3 | 19.2 | 95 | 80 |
| 4 | 18.6 | 87 | 82 |
| 5 | 20.2 | 136 | 136 |
| 6 | 30.2 | — | 15 |
| 7 | 8.8 | 117 | 120 |
| 9 | 14.6 | 78 | 54 |
| 11 | 51.9 | 51 | — |
| 12 | 9.3 | 119 | 113 |
| 14 | 8.5 | 81 | 19 |
| 16 | 52.6 | 104 | 64 |
| 17 | 16.8 | 102 | 44 |
| 18 | 8.0 | 113 | 105 |
| 20 | 10.2 | 114 | 117 |
| 21 | 5.4 | 99 | 109 |
| 23 | 27.0 | 115 | 102 |
| 25 | 18.7 | 86 | 72 |
| 26 | 9.7 | 61 | — |
| 28 | 67.6 | 113 | 83 |
| 29 | 24.6 | 14 | — |
| 30 | 119.0 | 94 | — |
| 31 | 36.8 | 107 | 35 |

The Example No. corresponds to the aforementioned Example.

TABLE 12

| Test compound (Example No.) | In Vitro IC$_{50}$ (nM) | In Vivo (%) allopurinol (3 mg/kg) | In Vivo (%) TMX-67 (0.3 mg/kg) |
|---|---|---|---|
| Example 8 | — | — | 125 |
| 10 | 22.6 | — | 84 |
| 13 | — | — | 141 |
| 24 | 18.5 | — | 28 |
| 27 | — | 36 | — |
| 32 | 9.2 | 81 | 38 |
| 33 | — | — | 48 |
| 35 | — | — | 61 |

TABLE 12-continued

| Test compound (Example No.) | In Vitro IC$_{50}$ (nM) | In Vivo (%) allopurinol (3 mg/kg) | In Vivo (%) TMX-67 (0.3 mg/kg) |
|---|---|---|---|
| 37 | 28.2 | — | 107 |
| 39 | 13.5 | — | 33 |
| 40 | — | 107 | 30 |
| 43 | — | — | 185 |
| 46 | 17.7 | — | 223 |
| 49 | 10.8 | — | 140 |

The Example No. corresponds to the aforementioned Example.

What is claimed is:

1. Compounds of the following formula (I) or salts thereof

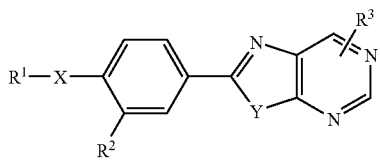

in which

R$^1$ represents an aryl group having 6-10 carbon atoms or a hetero-aryl group which may have a substituent selected from the group consisting of an alkyl group having 1-8 carbon atoms, a halogen-substituted alkyl group having 1-8 carbon atoms, an alkoxy group having 1-8 carbon atoms, an alkoxy group having 1-8 carbon atoms which is substituted with an alkoxy group having 1-8 carbon atoms, an alkoxycarbonyl group having 2-8 carbon atoms, formyl, carboxyl, halogen, hydroxyl, nitro, cyano, amino, an aryl group having 6-10 carbon atoms, and an aryloxy group having 6-10 carbon atoms;

R$^2$ represents cyano, nitro, formyl, carboxyl, carbamoyl, or an alkoxycarbonyl group having 2-8 carbon atoms;

R$^3$ represents hydroxyl, amino, carboxyl, mercapto, OR$^4$ or NHR$^5$ in which each of R$^4$ and R$^5$ is an alkyl group having 1-8 carbon atoms which may have a substituent selected from the group consisting of halogen, hydroxyl, nitro, cyano, amino, an aryl group having 6-10 carbon atoms, and an aryloxy group having 6-10 carbon atoms;

X represents oxygen, —N(R$^6$)—, or —S(O)$_n$— in which R$^6$ is hydrogen, an alkyl group having 1-8 carbon atoms, or the group for R$^1$, and n is an integer of 0 to 2; and Y represents sulfur.

2. The compounds or salts thereof defined in claim 1 in which R$^1$ represents a phenyl, naphthyl, furyl, pyrrolyl, thienyl, imidazolyl, pyrimidinyl, thiazolyl, pyridyl, indolyl or quinolyl group which may have a substituent selected from the group consisting of an alkyl group having 1-8 carbon atoms, a halogen-substituted alkyl group having 1-8 carbon atoms, an alkoxy group having 1-8 carbon atoms, an alkoxycarbonyl group having 2-8 carbon atoms, formyl, carboxyl, halogen, hydrocarbon, nitro, cyano, amino, an aryl group having 6-10 carbon atoms, and an aryloxy group having 6-10 carbon atoms.

3. The compounds or salts thereof defined in claim 1, in which R$^1$ represents a phenyl group which may have a substituent selected from the group consisting of an alkyl group having 1-8 carbon atoms, a halogen-substituted alkyl group having 1-8 carbon atoms, an alkoxy group having 1-8 carbon atoms, an alkoxycarbonyl group having 2-8 carbon atoms, formyl, carboxyl, halogen, hydroxyl, nitro, cyano, amino, an aryl group having 6-10 carbon atoms, and an aryloxy group having 6-10 carbon atoms.

4. The compounds or salts thereof defined in claim 1, in which R$^1$ represents a phenyl group which may have a substituent selected from the group consisting of an alkyl group having 1-8 carbon atoms, a halogen-substituted alkyl group having 1-8 carbon atoms, an alkoxy group having 1-8 carbon atoms, an alkoxycarbonyl group having 2-8 carbon atoms, formyl, carboxyl, halogen, phenyl, and phenoxy.

5. The compounds or salts thereof defined in claim 1, in which R$^2$ represents cyano or nitro.

6. The compounds or salts thereof defined in claim 1, in which R$^2$ represents cyano.

7. The compounds or salts thereof defined in claim 1, in which R$^3$ represents hydroxyl.

8. The compounds or salts thereof defined in claim 1, in which R$^3$ is attached to the 4-position of the condensed hetero ring.

9. The compounds or salts thereof defined in claim 1, in which X is oxygen, NH, or sulfur.

10. The compounds or salts thereof defined in claim 1, in which X is oxygen.

11. The compounds or salts thereof defined in claim 1, in which Y is sulfur.

12. A xanthine oxidase inhibitor containing as an active ingredient a compound or a salt thereof according to claim 1 and a suitable excipient or diluent.

13. An agent for treating hyperuricemia containing as an active ingredient a compound or a salt thereof according claim 1 and a suitable excipient or diluent.

* * * * *